ized Patent

United States Patent
Cho et al.

(10) Patent No.: US 10,627,362 B2
(45) Date of Patent: Apr. 21, 2020

(54) BLOOD GLUCOSE MEASURING DEVICE AND METHOD, AND ELECTRONIC DEVICE INCLUDING BLOOD GLUCOSE MEASURING MODULE

(71) Applicant: Samsung Electronics Co., Ltd., Gyeonggi-do (KR)

(72) Inventors: Seong-Je Cho, Gyeonggi-do (KR); Kwang-Bok Kim, Incheon (KR); Sun-Tae Jung, Gyeonggi-do (KR); Jae-Geol Cho, Gyeonggi-do (KR); Chul-Ho Cho, Gyeonggi-do (KR)

(73) Assignee: Samsung Electronics Co., Ltd (KR)

( * ) Notice: Subject to any disclaimer, the term of this patent is extended or adjusted under 35 U.S.C. 154(b) by 422 days.

(21) Appl. No.: 14/815,102

(22) Filed: Jul. 31, 2015

(65) Prior Publication Data
US 2016/0033440 A1 Feb. 4, 2016

(30) Foreign Application Priority Data

Jul. 31, 2014 (KR) ........................ 10-2014-0098554

(51) Int. Cl.
*G01N 27/327* (2006.01)
*G01N 33/49* (2006.01)

(52) U.S. Cl.
CPC ......... *G01N 27/3273* (2013.01); *G01N 33/49* (2013.01)

(58) Field of Classification Search
None
See application file for complete search history.

(56) References Cited

U.S. PATENT DOCUMENTS 6,773,671 B1 * 8/2004 Lewis ................... G01N 33/521
422/169
2007/0284444 A1 12/2007 Hellstrom et al.
2008/0097908 A1 4/2008 Dicks et al.
(Continued)

FOREIGN PATENT DOCUMENTS

CN 101421742 4/2009
CN 102472735 5/2012
(Continued)

OTHER PUBLICATIONS

European Search Report dated Jan. 19, 2016 issued in counterpart application No. 15178979.9-1408, 7 pages.
(Continued)

*Primary Examiner* — Jill A Warden
*Assistant Examiner* — Brittany I Fisher
(74) *Attorney, Agent, or Firm* — The Farrell Law Firm, P.C.

(57) ABSTRACT

A method and device for measuring blood glucose are provided. The device includes a strip receiving part having a plurality of pins therein, the pins being arranged in such a manner that at least one of the pins contacts at least one electrode formed in a blood glucose measurement strip when the blood glucose measurement strip is inserted into the strip receiving part; and a controller configured to identify a type of the blood glucose measurement strip inserted into the strip receiving part and to control application of a testing voltage configured in response to the identified type of the blood glucose measurement strip to each pin of the strip receiving part.

15 Claims, 21 Drawing Sheets

(56) References Cited

U.S. PATENT DOCUMENTS

| | | |
|---|---|---|
| 2009/0078588 A1 | 3/2009 | Lin et al. |
| 2010/0068093 A1* | 3/2010 | Wang ............... C12Q 1/006 422/400 |
| 2010/0094110 A1 | 4/2010 | Heiler et al. |
| 2011/0057671 A1* | 3/2011 | Welsh ............ G01N 33/48771 324/693 |
| 2011/0184264 A1* | 7/2011 | Galasso ............ A61B 5/14532 600/347 |
| 2012/0312082 A1 | 12/2012 | Elder |
| 2012/0312699 A1* | 12/2012 | Webster ............ G01N 27/3273 205/792 |
| 2013/0048495 A1 | 2/2013 | Charlton |
| 2013/0116526 A1 | 5/2013 | Javitt et al. |
| 2013/0175344 A1* | 7/2013 | Watanabe ......... G01N 21/8483 235/469 |
| 2013/0196446 A1* | 8/2013 | Groll ............... G01N 33/48771 436/150 |
| 2014/0131199 A1 | 5/2014 | Simmons et al. |
| 2014/0179151 A1* | 6/2014 | Carroll ................ H01R 12/613 439/377 |
| 2014/0374277 A1 | 12/2014 | Simmons et al. |

FOREIGN PATENT DOCUMENTS

| | | |
|---|---|---|
| CN | 102483400 | 5/2012 |
| CN | 203204001 | 9/2013 |
| KR | 1020130134866 | 12/2013 |
| TW | M422126 | 2/2012 |
| WO | WO 00/33074 | 6/2000 |

OTHER PUBLICATIONS

International Search Report dated Oct. 28, 2015 issued in counterpart application No. PCT/KR2015/007916, 12 pages.

Taiwanese Search Report dated Nov. 29, 2018 issued in counterpart application No. 104124621, 14 pages.

Chinese Office Action dated Aug. 30, 2018 issued in counterpart application No. 201510463454.7, 25 pages.

* cited by examiner

BLOOD GLUCOSE MEASURING DEVICE AND METHOD, AND ELECTRONIC DEVICE INCLUDING BLOOD GLUCOSE MEASURING MODULE

PRIORITY

This application claims priority under 35 U.S.C. § 119(a) to Korean Application Serial No. 10-2014-0098554, which was filed in the Korean Intellectual Property Office on Jul. 31, 2014, the entire content of which is incorporated herein by reference.

BACKGROUND OF THE INVENTION

1. Field of the Invention

The present invention relates generally to blood glucose measurement, and more particularly, to a blood glucose measuring device and method, and an electronic device including a blood glucose measuring module.

2. Description of the Related Art

Lately, improved living environments have caused an increase in adult diseases, and users, accordingly, have an increased interest in health. Among adult diseases, high blood pressure and diabetes are gradually increasing. Although people with such chronic diseases have to visit hospitals, they also have to periodically measure blood pressure and glucose themselves to frequently check their conditions, and take proper actions based on the measurements. For example, diabetic patients must monitor their blood glucose about six times a day in order to periodically measure their own blood glucose value and adjust the blood glucose value to a proper level.

Accordingly, portable personal medical devices, such as blood pressure gauges, blood glucose testers, insulin pumps, and the like, are rapidly spreading. According to the trend, standardization for such portable personal medical devices and services is being initiated. Further, personal medical devices and services utilizing personal medical are becoming more widely used.

Blood glucose can be easily measured using a blood glucose meter. The blood glucose meter takes a blood sample from a patient using a bio-sensor in the form of a sensor strip and measures a blood glucose value using an electric signal generated through an electrochemical reaction of the taken blood and a chemical substance in the bio-sensor.

According to the existing technologies, blood glucose meter manufacturers use different methods. Electrode arrangement, electrode intervals, and algorithms of strips (e.g., bio-sensor strips) for measuring blood glucose differ from each other according to the manufacturer. The same manufacturer may also use different methods for respective products. Therefore, users are only able to use only a dedicated strip that is appropriate for their own corresponding blood glucose meter.

Furthermore, since data measured through a blood glucose meter is not effectively managed, the users simply confirm some recently measured values. Moreover, the users must separately hold a blood glucose meter as a dedicated device in order to consistently measure and manage blood glucose.

SUMMARY OF THE INVENTION

The present invention is made to address at least the above-described problems and/or disadvantages and to provide at least the advantages described below. An aspect of the present invention is to provide a blood glucose measuring device and method and an electronic device including a blood glucose measuring module that can be used by manufacturing a different disposable blood glucose tester of each maker as a standardized module to be detachably coupled to one smart device and simply changing only the module in the same smart device.

Another aspect of the present invention is to provide a blood glucose measuring device and method that can identify strips of different manufacturers having different pin patterns, thereby measuring blood glucose irrespective of the manufacturer of the strip and/or the type of various strips produced by a single manufacturer.

According to an aspect of the present invention, a device for measuring blood glucose is provided. The device includes a strip receiving part having a plurality of pins therein, the pins being arranged in such a manner that at least one of the pins contacts at least one electrode formed in a blood glucose measurement strip when the blood glucose measurement strip is inserted into the strip receiving part; and a controller configured to identify a type of the blood glucose measurement strip inserted into the strip receiving part and to control application of a testing voltage configured in response to the identified type of the blood glucose measurement strip to each pin of the strip receiving part.

According to another aspect of the present invention, a method of measuring blood glucose is provided. The method includes determining whether a blood glucose measurement strip is inserted into a strip receiving part having a plurality of pins therein; identifying a type of the blood glucose measurement strip by at least one of the plurality of pins when the blood glucose measurement strip is inserted; and applying a testing voltage configured in response to the identified type of the blood glucose measurement strip to each pin of the strip receiving part.

According to another aspect of the present invention, an electronic device is provided. The electronic device includes a strip receiving part having a plurality of pins therein, the pins being arranged in such a manner that at least one of the pins contacts at least one electrode formed in a blood glucose measurement strip when the blood glucose measurement strip is inserted into the strip receiving part; a blood glucose measuring module configured to identify a type of the blood glucose measurement strip inserted into the strip receiving part and to control application of a voltage configured in response to the identified type of the blood glucose measurement strip to each pin of the strip receiving part; and a display unit configured to display blood glucose related information measured through the blood glucose measuring module.

According to another aspect of the present invention, a casing of an electronic device is provided. The casing includes a strip receiving part having a plurality of pins therein, the pins being arranged in such a manner that at least one of the pins contacts at least one electrode formed in a blood glucose measurement strip when the blood glucose measurement strip is inserted into the strip receiving part; a blood glucose measuring module configured to identify a type of the blood glucose measurement strip inserted into the strip receiving part and to control application of a voltage configured in response to the identified type of the blood glucose measurement strip to each pin of the strip receiving part; and a communication unit configured to transmit blood glucose related information measured through the blood glucose measuring module to the electronic device when the casing is coupled to the electronic device.

According to another aspect of the present invention, a device for checking a chemical test strip is provided. The device includes a strip receiving part having a plurality of pins therein, the pins being arranged in such a manner that at least one of the pins contacts at least one electrode formed in a chemical strip when the chemical strip is inserted into the strip receiving part; and a controller configured to identify a type of the chemical test strip inserted into the strip receiving part and controls application of a testing voltage configured in response to the identified type of the chemical test strip to each pin of the strip receiving part.

According to another aspect of the present invention, a casing of an electronic device is provided. The casing includes a strip receiving part having a plurality of pins therein, the pins being arranged in such a manner that at least one of the pins contacts at least one electrode formed in a blood glucose measurement strip when the blood glucose measurement strip is inserted into the strip receiving part; a blood glucose measuring module configured to detect, from the blood glucose measurement strip, first information that is differentiated according to a type of the blood glucose measurement strip; and a communication unit configured to transmit, to the electronic device, the detected information differentiated according to the type of the blood glucose measurement strip and to receive, from the electronic device, second information indicating a voltage to be applied according to the type of the blood glucose measurement strip, wherein the blood glucose measuring module applies the voltage to each pin of the strip receiving part according to the second information.

BRIEF DESCRIPTION OF THE DRAWINGS

The above and other aspects, features, and advantages of certain embodiments of the present invention will be more apparent from the following detailed description taken in conjunction with the accompanying drawings, in which.

Figure 1:
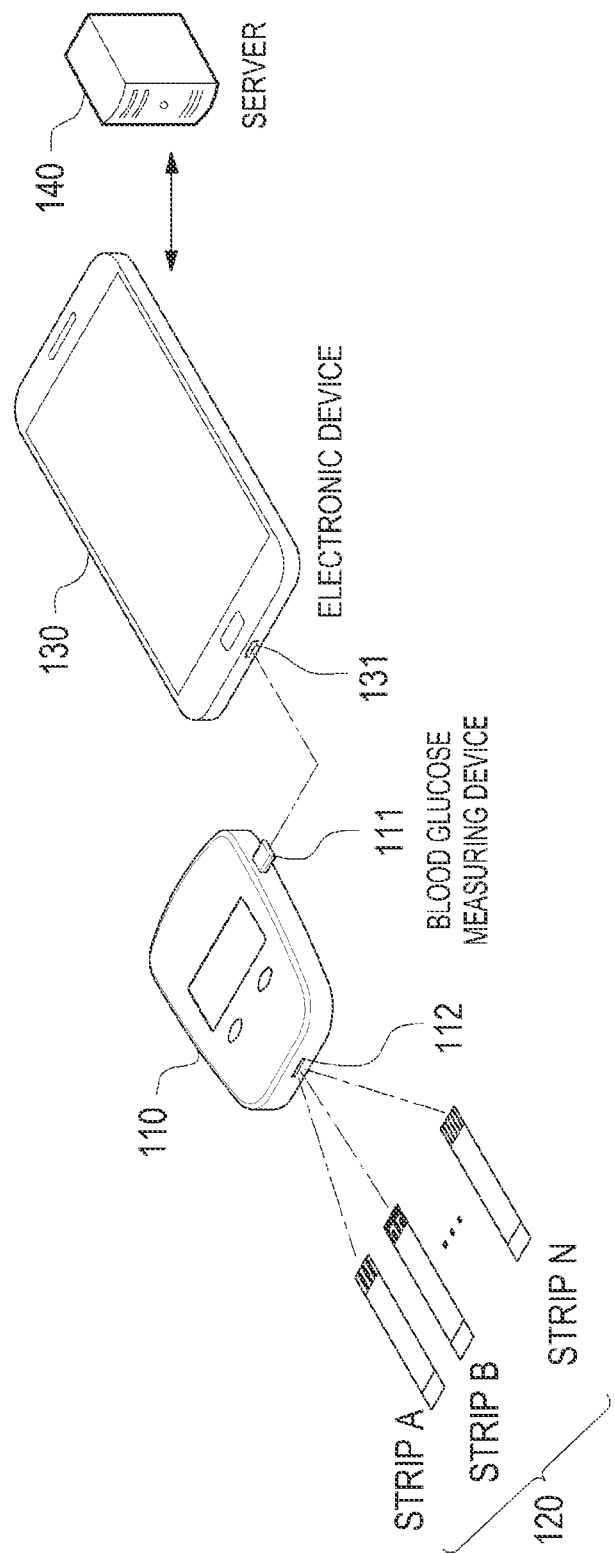
FIG. 1 is a diagram illustrating a connection relation of a blood glucose measuring device according to an embodiment of the present invention.

DETAILED DESCRIPTION OF EMBODIMENTS
OF THE PRESENT INVENTION

Various embodiments of the present invention described more fully in conjunction with the accompanying drawings. The present invention may include various embodiments, and modifications and changes may be made therein. However, embodiments of the present invention area not limited to the particular embodiments disclosed herein. As used in herein with respect to various embodiments of the present invention, the expressions "include", "may include" and other similar conjugates refer to the existence of a corresponding function, operation, or constituent element, and do not limit one or more additional functions, operations, or constituent elements. Further, as used with respect to various embodiments of the present invention, the terms "include", "have", and their conjugates are intended merely to denote a certain feature, numeral, step, operation, element, component, or a combination thereof, and should not be construed to initially exclude the existence of or a possibility of addition of one or more other features, numerals, steps, operations, elements, components, or combinations thereof.

In various embodiments of the present disclosure, the expression "or" or "at least one of A or/and B" includes any or all of combinations of words listed together. For example, the expression "A or B" or "at least A or/and B" may include A, may include B, or may include both A and B.

Meanwhile, expressions including ordinal numbers, such as "first" and "second", as used with respect to various embodiments of the present invention, may modify various constituent elements, such constituent elements are not limited by the above expressions. For example, the above expressions do not limit the sequence and/or importance of the elements. The expressions may be used to distinguish a component element from another component element. For example, a first user device and a second user device indicate different user devices, although both are user devices. For example, a first constituent element may be referred to as a second constituent element, and likewise a second constituent element may also be referred to as a first constituent element without departing from the scope of various embodiments of the present invention.

If a component element is described as "coupled" or "connected" to another component element, the first component element may be directly coupled or connected to the second component, and a third component element may be "coupled" or "connected" between the first and second component elements. Conversely, when one component element is "directly coupled" or "directly connected" to another component element, a third component element does not exist between the first component element and the second component element.

The term "module" as used herein with respect to embodiments of the present disclosure may refer to, for example, a unit including one of hardware, software, and firmware or any combination thereof. The term "module" may be interchangeably used with a term such as unit, logic, logical block, component, or circuit. The term "module" may refer to the smallest unit of an integrated component or a part thereof. The term "module" may refer to the smallest unit that performs one or more functions or a part thereof. A module may be mechanically or electronically implemented. For example, a module according to an embodiment of the present invention may include an Application-Specific Integrated Circuit (ASIC) chip, a Field-Programmable Gate Array (FPGA), and a programmable-logic device for performing certain operations currently known or to be developed hereafter.

The terms as used herein with respect to various embodiments of the present invention are merely used for the purpose of describing particular embodiments and are not intended to limit the embodiments of the present invention. As used herein, the singular forms are intended to include the plural forms as well, unless the context clearly indicates otherwise.

Unless defined otherwise, all terms used herein, including technical terms and scientific terms, have the same definition as commonly understood by a person of ordinary skill in the art to which various embodiments of the present invention pertain. Such terms as those defined in a generally used dictionary are to be interpreted to have the same definitions as the contextual definitions in the relevant field of art, and are not to be interpreted to have ideal or excessively formal definitions unless clearly defined with respect to embodiments of the present invention.

A blood glucose measuring device or an electronic device according to embodiments of the present invention may include, but is not limited to, a device including a communication function. For example, the electronic device may include a smartphone, a tablet Personal Computer (PC), a mobile phone, a video phone, an electronic book (e-book) reader, a desktop PC, a laptop PC, a netbook computer, a Personal Digital Assistant (PDA), a Portable Multimedia Player (PMP), an MP3 player, a mobile medical appliance, a camera, or a wearable device (e.g. a Head-Mounted-Device (HMD), such as electronic glasses, electronic clothes, an electronic bracelet, an electronic necklace, an electronic appcessory, electronic tattoos, or a smartwatch).

According to some embodiments of the present invention, the blood glucose measuring device or the electronic device may be a smart home appliance. A smart home appliance, as an example of an electronic device, may include for example, a television, a Digital Video Disk (DVD) player, an audio system, a refrigerator, an air conditioner, a vacuum cleaner, an oven, a microwave oven, a washing machine, an air cleaner, a set-top box, a TV box (e.g., Samsung HomeSync™, Apple TV™, or Google TV™), a game console, an electronic dictionary, an electronic key, a camcorder, or an electronic picture frame.

According to some embodiments of the present invention, the entity may include any of various medical appliances (e.g., Magnetic Resonance Angiography (MRA), Magnetic Resonance Imaging (MRI), Computed Tomography (CT), and ultrasonic machines), navigation equipment, a Global Positioning System (GPS) receiver, an Event Data Recorder (EDR), a Flight Data Recorder (FDR), an in-vehicle infotainment device, electronic equipment for ships (e.g., ship navigation equipment and a gyrocompass), avionics, security equipment, a vehicle head unit, an industrial or home robot, an Automatic Teller Machine (ATM) of a banking system, or a Point of Sales (POS) of a store.

According to some embodiments of the present invention, the electronic device may include a part of furniture or a building/structure having a communication function, an electronic board, an electronic signature receiving device, a projector, or various kinds of measuring instruments (e.g., a water meter, an electric meter, a gas meter, a radio wave meter, and the like). An electronic device according to various embodiments of the present invention may be a combination of one or more of the aforementioned various devices. Further, an electronic device according to various embodiments of the present invention may include a flexible device. Further, an electronic device according to various embodiments of the present invention is not limited to the aforementioned devices.

According to an embodiment of the present invention, a blood glucose measuring device may be implemented in the form of a separate independent device or in the form of a module in an arbitrary electronic device.

Hereinafter, a blood glucose measuring device or an electronic device including a blood glucose measuring module, according to various embodiments of the present invention, is described with reference to the accompanying drawings. The term "user" as used with respect to various embodiments of the present invention may refer to a person using an electronic device or a device (e.g., an artificial intelligence electronic device) using an electronic device.

FIG. 1 illustrates a connection relation of a blood glucose measuring device according to an embodiment of the present invention.

Referring to FIG. 1, the blood glucose measuring device 110, according to an embodiment of the present invention, may be manufactured in the form of an independent device having a separate casing or may be included in the form of a blood glucose measuring module in an electronic device.

The blood glucose measuring device 110 includes a strip receiving part 112 into which each of strips 120 (e.g., a biosensor strip for measuring blood glucose and hereinafter referred to as 'strip') is inserted. According to an embodiment of the present invention, when each of the strips 120 is inserted into the strip receiving part 112, a determination of whether the strip 120 is inserted into the strip receiving part 112 is performed, and the type of the strip 120 is identified, thereby enabling the blood glucose measuring device 110 to measure blood glucose using various different types of strips 120. A method of identifying the type of the strip 120 is described herein below with reference to the related drawings.

After the strip 120 is inserted into the strip receiving part 112 of the blood glucose measuring device 110 and the type of inserted strip 120 is identified, blood glucose is measured by applying a voltage to the strip 120.

The blood glucose measuring device 110 may be connected to a connector 131 of an electronic device 130 via a connector 111 that may be connected to an external device through communication. The blood glucose measuring device 110 and the electronic device 130 may be interconnected through a direct connection between the connectors thereof or through a separate cable (e.g., a Universal Serial Bus (USB) cable). Data related to the blood glucose measured by the blood glucose measuring device 110 may be transmitted to the electronic device 130 connected via a wired or wireless communication unit. In addition, the blood glucose related data (e.g., the measured blood glucose value, the date and time when the blood glucose was measured, empty-stomach related information, and the like) received by the electronic device 130 may be transmitted to a server 140 and managed therein.

Figure 2:
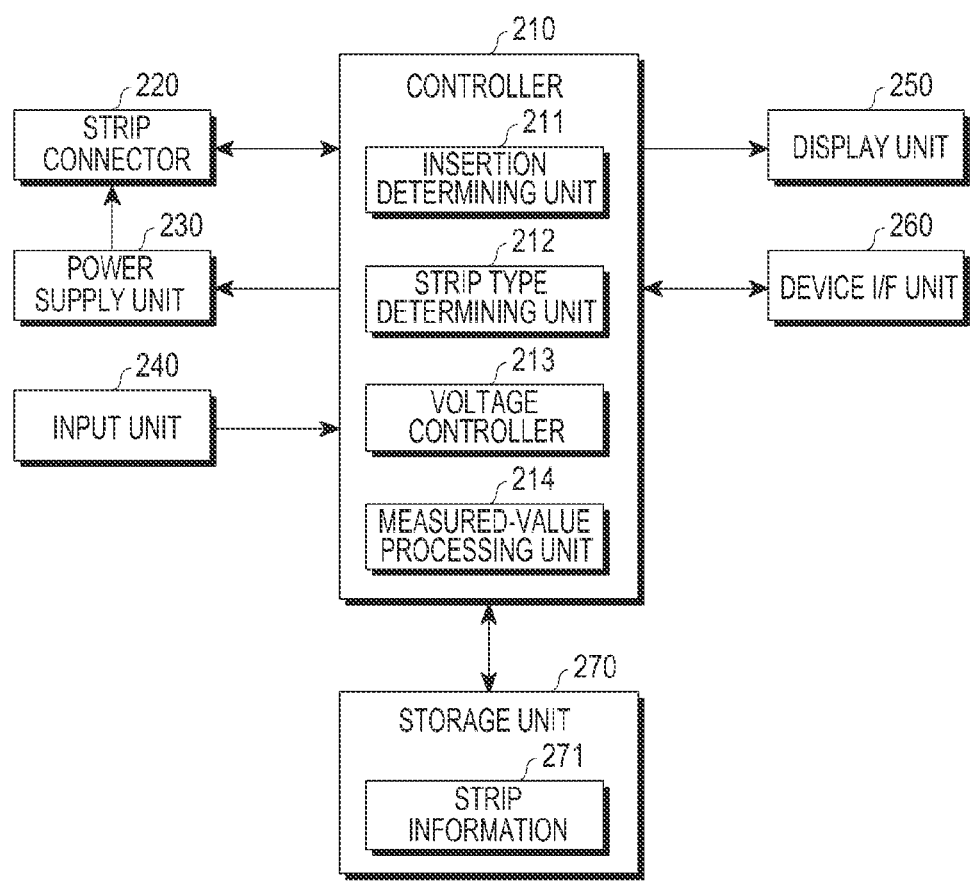
FIG. 2 is a block diagram illustrating a detailed structure of a blood glucose measuring device according to an embodiment of the present invention.

FIG. 2 is a block diagram illustrating a detailed structure of a blood glucose measuring device according to an embodiment of the present invention.

Referring to FIG. 2, a blood glucose measuring device according to an embodiment of the present invention includes a controller 210, a strip connector 220, a power supply unit 230, an input unit 240, a display unit 250, a device InterFace (I/F) unit 260, and a storage unit 270. In addition, the controller 210 includes an insertion determining unit 211, a strip type determining unit 212, a voltage controller 213, and a measured-value processing unit 214.

When a strip is inserted through the strip connector 220, the insertion determining unit 211 of the controller 210 determines whether the strip is inserted. At this time, the insertion determining unit 211 may also determine a degree of insertion of the strip (e.g., may determine whether the strip is partially or completely inserted through the strip connector 220). Notification information indicating whether the strip is inserted may be output to a user through the display unit 250.

When the insertion determining unit 211 determines that the strip has been completely inserted, the voltage controller 213 controls the power supply unit 230 to supply power to the strip connector 220 in order to determine the type of the strip. When power is supplied from the power supply unit 230 to the strip connector 220, the strip type determining unit 212 checks a voltage or current detected through each pin of the strip connector 220 and identifies the pattern of the inserted strip with reference to strip information 271 stored in the storage unit 270. In addition, when a plurality of types of strips share the same pattern, the strip type determining unit 212 may measure the resistance of each pin to identify the types of the strips (e.g., strip makers or model names).

When the type of inserted strip is identified, the voltage controller 213 identifies the strip information 271 stored in the storage unit 270. The strip information 271 may include information, such as an electrode type (a dual electrode type or a triple electrode type), an operating voltage, an operating electrode, a counterpart electrode, a standard electrode, and the like, which have been set for each maker or model name.

The voltage controller 213 checks a voltage to apply to each pin with reference to the identified strip information 271 and controls the power supply unit 230 to apply the voltage corresponding to the identified strip to each pin of the strip connector 220.

The measured-value processing unit 214 estimates a blood glucose value, for example, by comparing a voltage of current flowing through each pin of the strip connector 220 with a reference value corresponding to each strip type.

The input unit 240 may include a power button for turning on or off the blood glucose measuring device, and a button for inputting each setting value. The display unit 250 may display the operating state, the measured value, and the like of the blood glucose measuring device. The device I/F unit 260 may be connected to an external device according to a set communication scheme to transmit and receive data.

At least some elements of the blood glucose measuring device illustrated in FIG. 2 may be omitted for simplification of the device in accordance with embodiments of the present invention. For example, as illustrated in FIG. 1, the blood glucose measuring device may be connected to an external electronic device through the device I/F unit 260, and the external electronic device may provide at least some functions of the blood glucose measuring device.

For example, at least one of the power supply unit 230, the input unit 240, the display unit 250, and the storage unit 270 of the blood glucose measuring device may be omitted, and when the blood glucose measuring device is connected to an external electronic device (e.g., a smart phone) through the device I/F unit 260, the connected electronic device may provide the functions corresponding to the omitted elements.

In addition, according to an embodiment of the present invention, the connected external electronic device may also perform portions of operations performed by elements of the blood glucose measurement device. For example, the connected external electronic device may perform a determination of the type of blood glucose measurement strip based on pin pattern information received from the blood glucose measurement device.

In addition, according to an embodiment of the present invention, the power supply unit 230 of the blood glucose measuring device may supply power using various types of batteries, such as a rechargeable battery, a battery, a solar battery, and the like. The power supply unit 230 may also be omitted for simplification of the device. For example, when the blood glucose measuring device is connected to an external electronic device, power may be supplied from the connected electronic device, and the blood glucose measuring device may operate using the power supplied from the electronic device.

Figure 3:
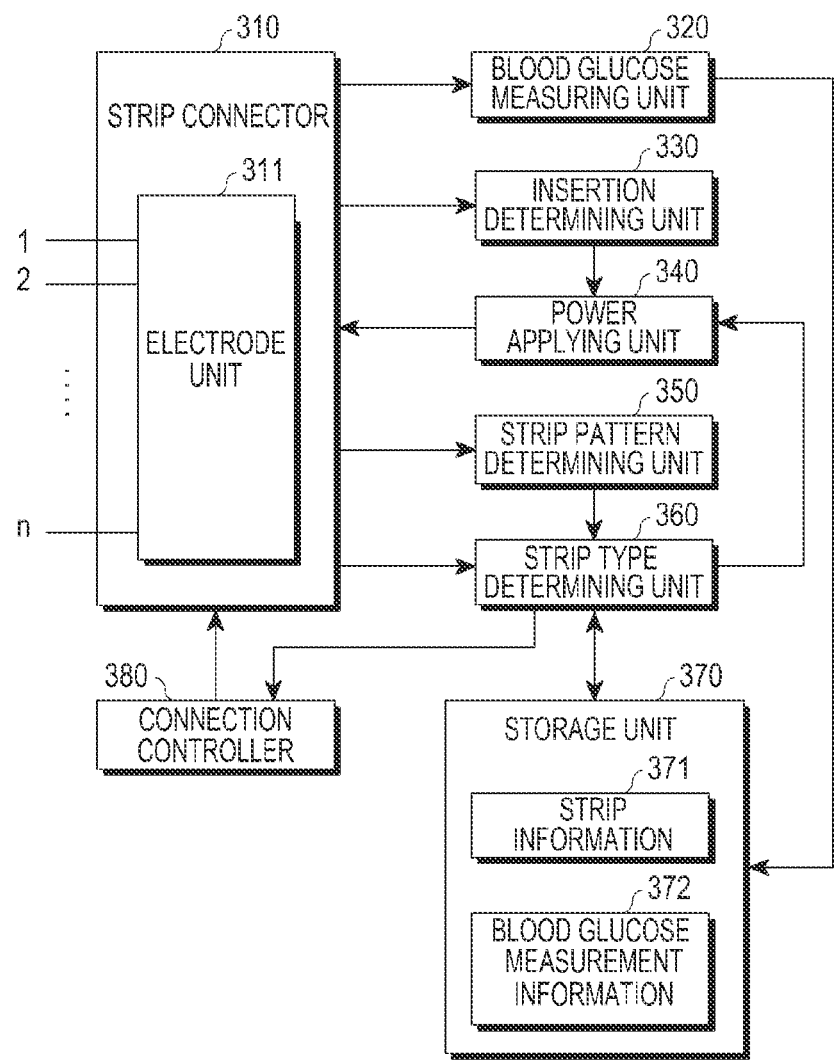
FIG. 3 is a block diagram illustrating a detailed structure of a blood glucose measuring device according to an embodiment of the present invention.

FIG. 3 is a block diagram illustrating a detailed structure of a blood glucose measuring device according to an embodiment of the present invention.

Referring to FIG. 3, the blood glucose measuring device, according to an embodiment of the present invention, includes a strip connector 310, a blood glucose measuring unit 320, an insertion determining unit 330, a power applying unit 340, a strip pattern determining unit 350, a strip type determining unit 360, a storage unit 370, and a connection controller 380.

When a strip is inserted through the strip connector 310, the insertion determining unit 330 determines whether the strip is inserted. At this time, the insertion determining unit 330 may also determine a degree of insertion of the strip (e.g., determine whether the strip is partially or completely inserted through the strip connector 310). When the insertion determining unit 330 determines that the strip has been completely inserted, the power applying unit 340 supplies power to an electrode unit 311 of the strip connector 310 in order to determine the type of the strip.

According to an embodiment of the present invention, an electrode of the strip makes contact with at least one of a number 'n' electrodes (e.g., ten electrodes) included in the strip connector 310, and the strip pattern determining unit 350 determines the pattern of the strip by determining which of the n electrodes (e.g., which of the ten electrodes) contacts the electrode of the strip.

The strip type determining unit 360 identifies the type of the strip (e.g., the strip maker or model name) corresponding to the pattern of the inserted strip with reference to strip information 371 stored in the storage unit 370.

According to an embodiment of the present invention, when a plurality of types of strips have the same pattern as the strip, the strip type determining unit 360 measures the resistance of each pin of the electrode unit 311 to accurately identify the types of strips (e.g., the makers or model names of the strips).

When the type of the inserted strip is identified, the power applying unit 340 identifies the strip information 371 stored in the storage unit 370 and supplies a voltage corresponding to the strip information 371 to at least one corresponding pin among the electrode pins of the electrode unit 311.

For example, the connection controller 380 controls a connection to apply a voltage to the electrodes of the strip connector 310, which are connected to the strip electrodes inserted into the strip connector 310, among the plurality of electrodes of the strip connector 310.

The blood glucose measuring unit 320 measures a blood glucose value by comparing a voltage of current flowing through each pin of the electrode unit 311 included in the strip connector 310 with a reference value corresponding to each strip type. The blood glucose measurement information 372 measured by the blood glucose measuring unit 320 is stored in the storage unit 370.

A device for measuring blood glucose, according to an embodiment of the present invention, may include a strip receiving part having a plurality of pins therein, the pins being arranged in such a manner that at least one of the pins contacts at least one electrode formed in a strip for blood glucose measurement when the strip is inserted into the strip receiving part; and a controller that identifies the type of strip for blood glucose measurement which is inserted into the strip receiving part and makes a control to apply a voltage configured in response to the identified type of strip to each pin of the strip receiving part.

According to an embodiment of the present invention, the controller detects at least one pin contacting at least one electrode of the strip for blood glucose measurement among the plurality of pins to identify the type of strip for blood glucose measurement.

According to an embodiment of the present invention, the controller controls application of a voltage for identifying the type of strip to the plurality of pins when the strip is inserted into the strip receiving part.

According to an embodiment of the present invention, the controller controls identification of the type of strip in further consideration of resistance values measured from the plurality of pins.

According to an embodiment of the present invention, the plurality of pins move in a direction opposite to the protruding direction thereof as the strip is inserted into the strip receiving part, and the controller controls detections of the movement of the pins and determines whether the strip is inserted accordingly.

According to an embodiment of the present invention, the plurality of pins are divided into a first pin group disposed on an outer side of the strip receiving part and a second pin group disposed on an inner side of the strip receiving part, and the controller detects a movement of at least one pin in the first pin group to determine whether the strip is inserted and detect a movement of at least one pin in the second pin group to determine whether the strip is completely inserted.

According to an embodiment of the present invention, the controller applies a voltage configured in response to the identified type of strip to at least one pin contacting an electrode of the strip.

According to an embodiment of the present invention, the device may further include a connector that communicates with an electronic device, and the device receives power from the electronic device through the connector.

Figure 4:
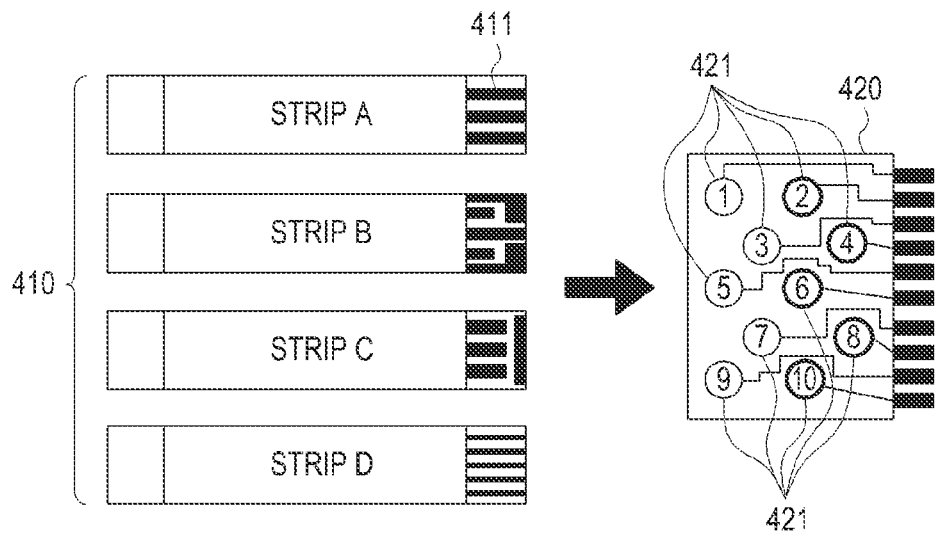
FIG. 4 is a diagram illustrating a strip pattern identification concept according to an embodiment of the present invention.

FIG. 4 is a diagram illustrating a strip pattern identification concept according to an embodiment of the present invention.

Referring to FIG. 4, strips 410 manufactured by various manufacturers have different electrode patterns 411.

According to an embodiment of the present invention, a number 'n' pins 421 (e.g., ten pins) are formed in a strip connector 420 of a blood glucose measuring module into which a strip is inserted. The positions of the pins may be set in various manners. For example, from among all the pins 421, some pins (e.g., pins 1, 3, 5, 7, and 9 in FIG. 4) may be disposed on an entrance side of the strip receiving part into which the strip is inserted, and the other pins (e.g., pins 2, 4, 6, 8, and 10) may be disposed close to an inner side of the strip receiving part.

Accordingly, when each of the strips 410 is inserted into the strip connector 420, the insertion of the strip 410 may be first detected by the pins disposed on the entrance side, and when the strip 410 is completely inserted into the strip connector 420, it may be detected by the pins disposed on the inner side of the strip receiving part that the strip is completely inserted.

When the strip 410 is completely inserted, the electrodes formed in the strip 410 are connected to one or more pins 421 disposed in the strip connector 420. At this time, since the electrode patterns 411 of the strips 410 are different from each other, pin numbers of the connected pins 421 vary according to the type of the inserted strip 410. In this way, the type of the strip 410 may be identified by identifying the pin numbers of the pins 421 connected to the electrodes 411 of the strip.

For example, when the strip 410 is completely inserted into the strip connector 420 as described above, power is applied to each of the pins 421 of the strip connector 420, and the electrode 411 of the strip 410 and at least one of the pins 421 contact each other so that a current flows in at least one of the plurality of pins 421. The type of the strip 410 may be determined by identifying the at least one pin through which current flows.

Referring to FIG. 4, when the strip 410 is inserted into the strip connector 420, at least one electrode 411 formed in the strip 410 contacts at least one of the plurality of pins 421 (e.g., ten pins) disposed in the strip connector 420.

When a voltage for identifying the type of the strip 410 is applied to each pin 421 of the strip connector 420, the arrangement and/or pattern of the electrodes may be identified by measuring resistances between pins 1 and 2, pins 3 and 4, pins 5 and 6, pins 7 and 8, and pins 9 and 10. The maker and model name of the strip may be identified by the identified arrangement and/or pattern of the electrodes.

According to the identified type of the strip, a dual or triple electrode type, an operating voltage, an operating electrode, a counterpart electrode, a standard electrode, and the like may be determined for each maker/model.

In addition, according to an embodiment of the present invention, for each strip model, a particular operating voltage may be applied to a particular electrode, and a measured value may be obtained from a predetermined electrode, using a previously made table, such as Table 1 below.

TABLE 1

| Strip | Electrode Type | Operating Electrode | Counterpart Electrode | Standard Electrode | Operating Voltage [mV] |
|---|---|---|---|---|---|
| A | 3 | 5 | 9 | 1 | 400 |
| B | 2 | 1 | 9 | X | 250 |
| C | 3 | 1 | 9 | 5 | 350 |
| D | 3 | 2 | 6 | 10 | 300 |
| . | . | . | . | . | . |
| . | . | . | . | . | . |
| . | . | . | . | . | . |
| Z | 3 | 5 | 9 | 1 | 200 |

Although FIG. 4 depicts ten pins 421 disposed in the strip connector 420, a different number of pins than illustrated in FIG. 4 may also be disposed in the strip connector 420 in accordance with embodiments of the present invention. In addition, according to an embodiment of the present invention, the electrode arrangement may be arbitrarily selected, and for a simple configuration of hardware, the arrangement of triple electrodes may be maintained identically if possible.

Used electrodes (i.e., electrodes to be used in performing glucose measurement) and an electrode configuration identifying method for each strip type may be identified, for example, according to Table 2 below.

TABLE 2

| Strip Type | Used electrodes according to measurement methods | | Electrode configuration identifying method |
|---|---|---|---|
| | Triple electrode type | Duel electrode type | |
| A | 1-5-9 | $_3C_2 = 3$ | 1-2/3-4/5-6/7-8/9-10 |
| B | $_5C_3 = 10$ | $_5C_2 = 10$ | Measure resistance between electrodes |
| C | 1-5-9 | $_3C_2 = 3$ | |
| D | $_5C_3 = 10$ | $_5C_2 = 10$ | |

Figure 5:
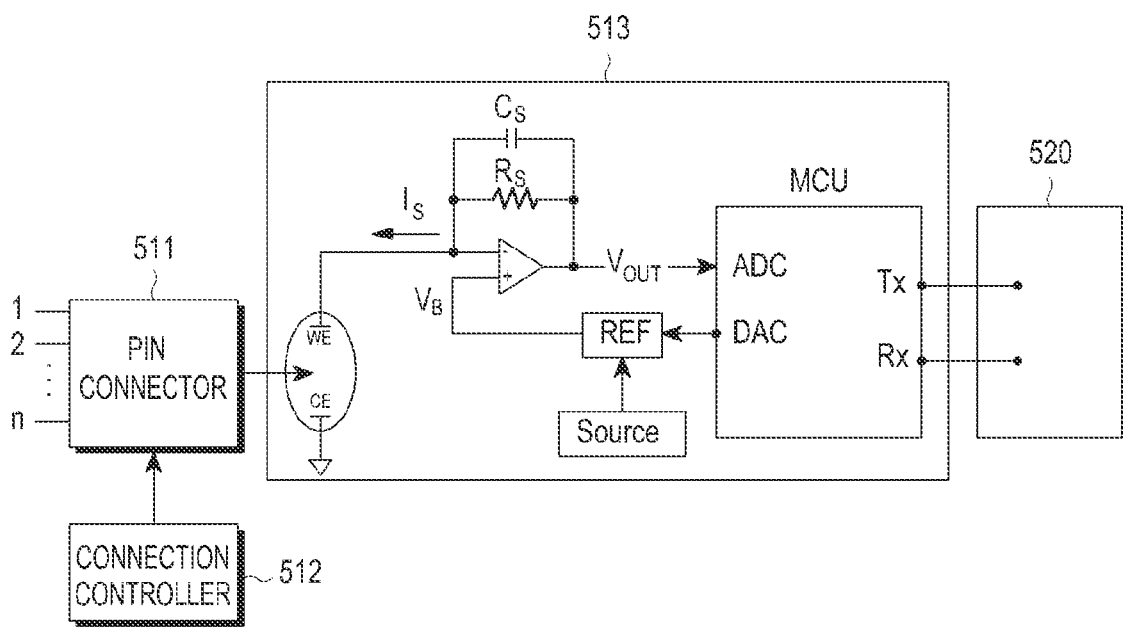
FIG. 5 is circuit diagram illustrating a blood glucose measuring unit according to an embodiment of the present invention.
Figure 6:
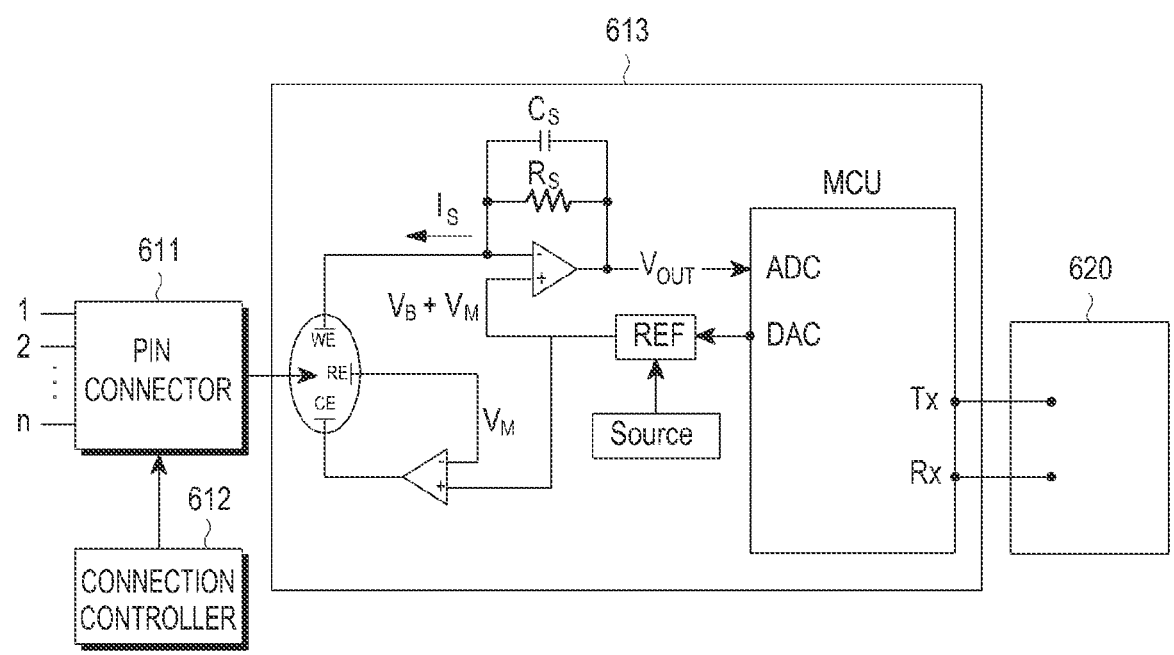
FIG. 6 is a circuit diagram illustrating a blood glucose measuring unit according to an embodiment of the present invention.

FIGS. 5 and 6 are detailed circuit diagrams of blood glucose measuring units according to embodiments of the present invention.

Referring to FIGS. 5 and 6, when a strip is inserted into a blood glucose measuring device and the type of the strip is determined as described above, the blood glucose measuring device measures blood glucose by applying power to a strip connector.

For example, power is applied to a pin connected to an electrode of the strip among a number 'n' pins according to the identified strip type, and a connection controller 512 or 612 supplies a current from the pin to which the power is applied among the n pins to a blood glucose measuring unit 513 or 613.

As illustrated, the blood glucose measuring unit 513 or 613 compares a voltage measured from each pin with a reference voltage through a comparator to measure a blood glucose value. Analog data of the measured blood glucose value may be converted into digital data through a Micro Control Unit (MCU), and the blood glucose value converted into the digital data is transmitted to an external electronic device 520 or 620.

In addition, according to some embodiments of the present invention, when the blood glucose measuring device is connected to the external electronic device 520 or 620, power may be supplied from the electronic device 520 or 620 to the blood glucose measuring unit 513 or 613 of the blood glucose measuring device as described above. The blood glucose measuring unit 513 or 613 may measure the blood glucose value using the power supplied from the electronic device 520 or 620.

FIG. 5 illustrates a dual electrode type blood glucose measuring device according to an embodiment of the present invention, and FIG. 6 illustrates a triple electrode type blood glucose measuring device according to an embodiment of the present invention.

The blood glucose measuring device and the external electronic device 520 or 620 may be connected to each other through a variety of communication schemes. For example, a typical wired communication scheme, such as Universal Asynchronous Receiver-Transmitter (UART), Serial Peripheral Interface (SPI), Inter-Integrated Circuit (I2C), or the like, may be used in data communication between a standardized module and an electronic device (e.g., a smart phone).

Figure 7:
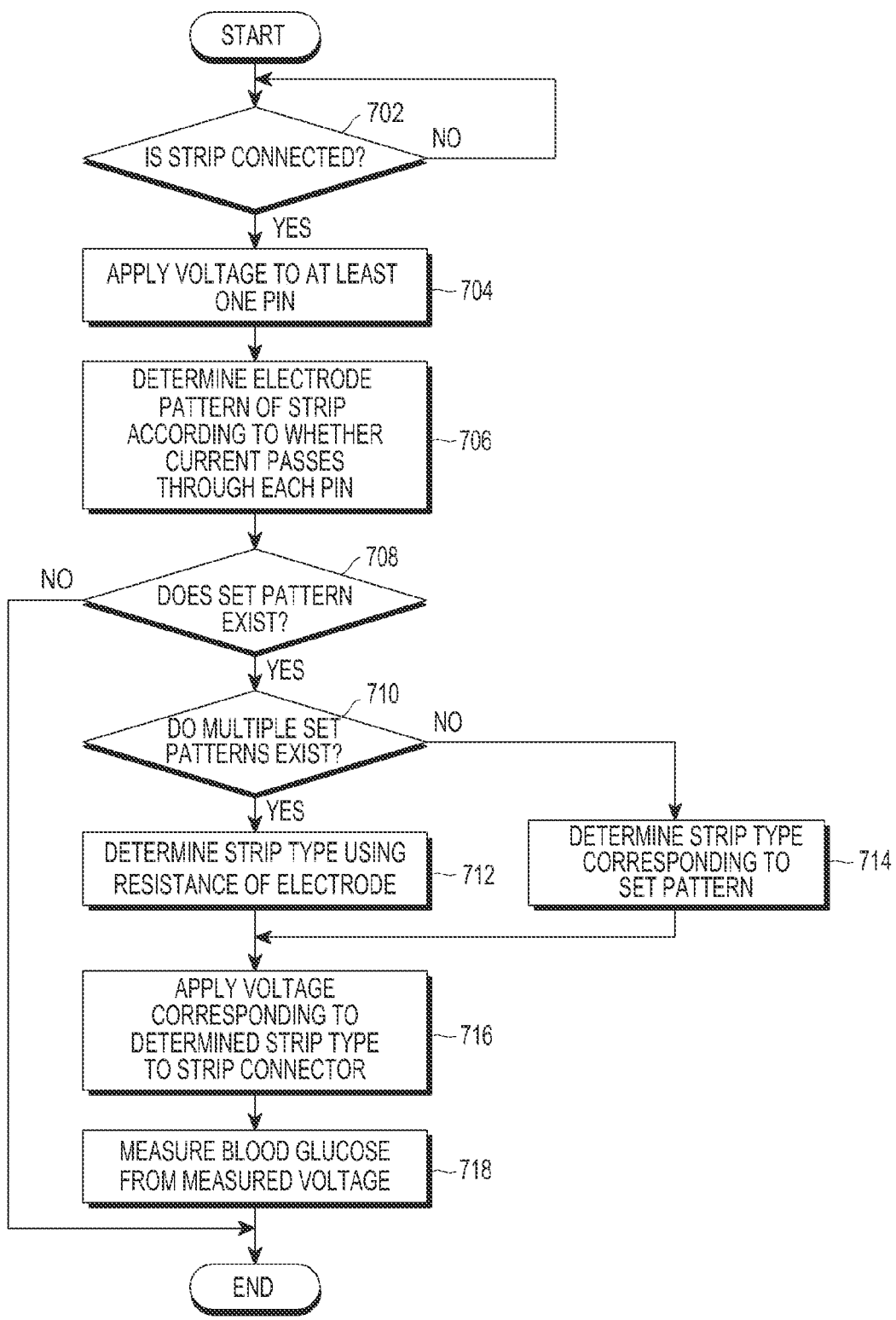
FIG. 7 is a flowchart illustrating a procedure of measuring blood glucose according to an embodiment of the present invention.

FIG. 7 is a flowchart illustrating a procedure of measuring blood glucose according to an embodiment of the present invention.

Referring to FIG. 7, when a strip is connected to (or inserted into) a strip connector of a blood glucose measuring device, in step 702, power is applied to at least one pin included in the strip connector, in step 704.

In step 706, the electrode pattern of the strip is determined according to whether a current passes through each pin. When it is determined in step 708 that a set pattern exists, the blood glucose measuring device, in step 710, determines whether a plurality of set patterns corresponding to the determined electrode pattern exists. When it is determined that one set pattern exists, the blood glucose measuring device determines the type of the strip corresponding to the set pattern, in step 714.

In contrast, when it is determined that a plurality of set patterns corresponding the determined electrode pattern exists, the blood glucose measuring device determines the type of the strip by measuring the resistance of each electrode, in step 712.

When the type of the strip is determined as described above, the blood glucose measuring device applies a voltage corresponding to the determined strip type to the strip connector, in step 716.

In step 718, the blood glucose measuring device measures blood glucose using the voltage measured from each pin of the strip connector.

A method of measuring blood glucose, according to an embodiment of the present invention, may include determining whether a strip for blood glucose measurement is inserted into a strip receiving part having a plurality of pins therein; identifying the type of strip for blood glucose measurement by at least one of the pins when the strip for blood glucose measurement is inserted; and applying a voltage configured in response to the identified type of strip to each pin of the strip receiving part.

According to an embodiment of the present invention, the type of strip for blood glucose measurement is identified by detecting at least one pin contacting at least one electrode of the strip for blood glucose measurement among the plurality of pins.

According to an embodiment of the present invention, the method further includes applying a voltage for identifying the type of strip to the plurality of pins when the strip is inserted into the strip receiving part.

According to an embodiment of the present invention, the type of strip is identified in further consideration of resistance values measured from the plurality of pins.

According to an embodiment of the present invention, the plurality of pins move in a direction opposite to the protruding direction thereof, as the strip is inserted into the strip receiving part, and the method further includes detecting movement of the pins to determine whether the strip is inserted.

According to an embodiment of the present invention, the plurality of pins is divided into a first pin group disposed on the outer side of the strip receiving part and a second pin group disposed on the inner side of the strip receiving part, and the method further includes detecting movement of at least one pin in the first pin group to determine whether the strip is inserted and detecting movement of at least one pin in the second pin group to determine whether the strip is completely inserted.

According to an of the present invention, the method further includes applying the voltage configured in response to the identified type of strip to at least one pin contacting an electrode of the strip.

Figure 8:
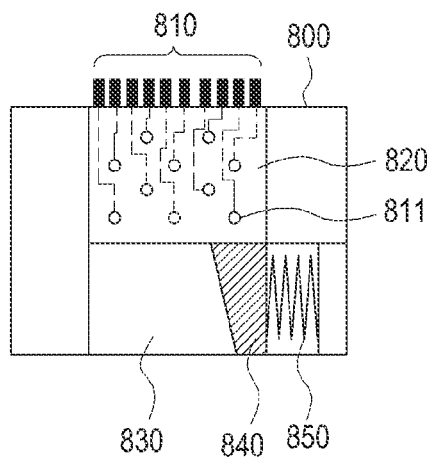
FIGS. 8, 9, and 10 are diagrams illustrating strip connectors into which a strip is inserted, according to embodiments of the present invention.
Figure 9:
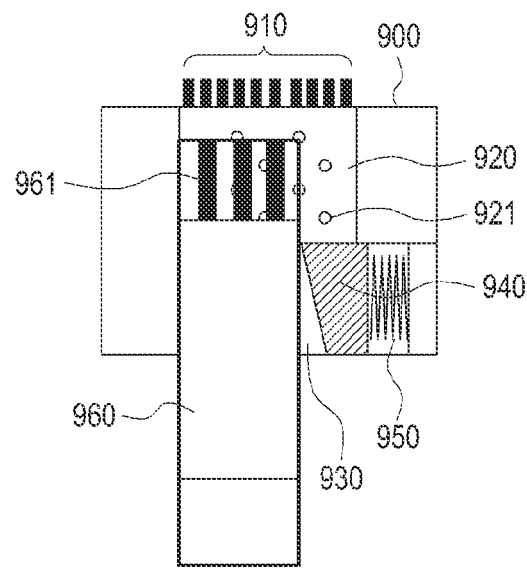
Figure 10:
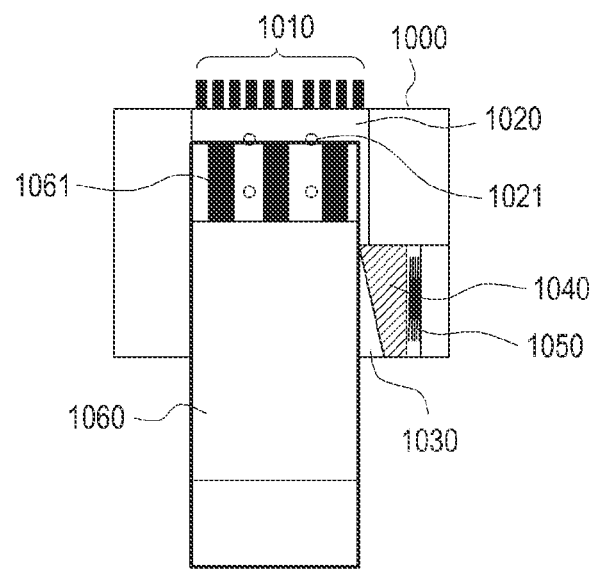

FIGS. 8, 9, and 10 illustrate strip connectors into which a strip is inserted, according to an embodiment of the present invention.

Referring to FIGS. 8, 9, and 10, a strip connector 800, 900, or 1000 includes a receiving part 820, 920, or 1020, respectively, in which a respective plurality of pins 811, 921, or 1021 connected to a respective plurality of pin connection parts 810, 910, or 1010 are disposed.

The arrangement form of the plurality of pins 811 (e.g., ten pins in FIG. 8) may vary, and the pins 811 may be arranged to efficiently identify electrode patterns of various types of strips.

In addition, among the plurality of pins 811, at least some pins (e.g., pins 1, 3, 5, 7, and 9 in FIG. 4) may be disposed on the entrance side of the receiving part 820 into which a strip is inserted, and the other pins (e.g., pins 2, 4, 6, 8, and 10 in FIG. 4) may be disposed close to the inner side of the receiving part 820.

The receiving part 820 is a space for receiving a part of the strip in which the electrode pattern is formed, when the strip is completely inserted into the strip connector 800.

A guide part 830 allows a strip 960 or 1060 to be aligned with one surface thereof (e.g., a left side surface) when the strip 960 or 1060 is inserted into the strip connector 800 as illustrated. For example, as illustrated in FIGS. 8 to 10, as the strip 960 or 1060 begins to be inserted into the guide part 830, 930, or 1030, a guide member 840, 940, or 1040 pushes the inserted strip 960 or 1060 to a side (e.g., the left side) of the guide part via a force provided by a resilient member 850, 950, or 1050 placed on a side (e.g., the right side) of the guide part 830, 930, or 1030, so that the inserted strip 960 or 1060 is aligned to the side (e.g., the left) of the guide part.

If the inserted strip 960 or 1060 is aligned with the side (e.g., the left) of the guide part as described above, an electrode 961 or 1061 of the strip may contact the same pin (e.g., pin 811, 921, or 1021) whenever the same strip is inserted.

According to some embodiments of the present invention, referring to FIGS. 9 and 10, the strips 960 and 1060 have different electrode patterns in contact with the different pins 811, 921, and 1021 when being inserted into the strip connector 800, 900, and 1000. Due to this difference, it is possible to identify patterns for various types of strips.

Figure 11A:
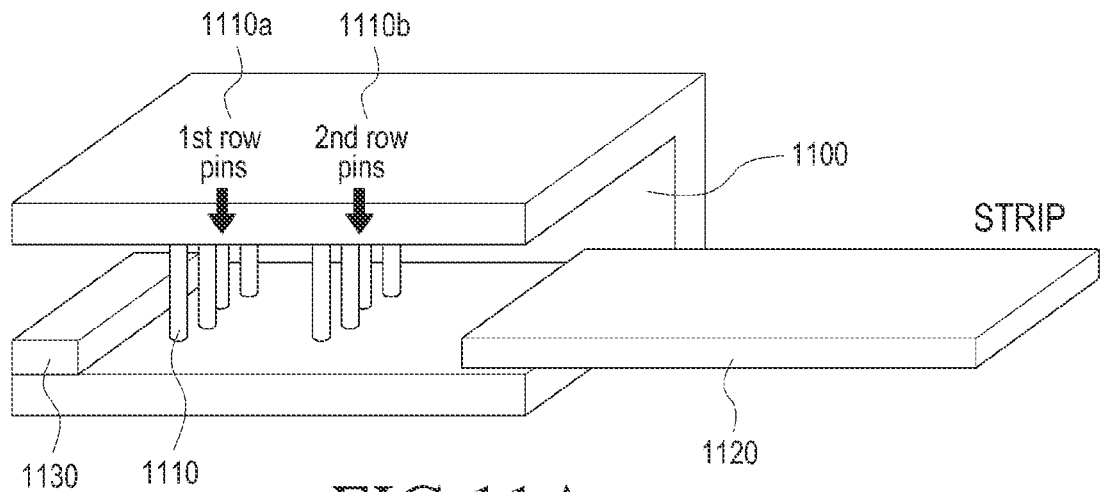
FIGS. 11A, 11B, and 11C are diagrams illustrating a process of inserting a strip into a strip connector according to an embodiment of the present invention.
Figure 11B:
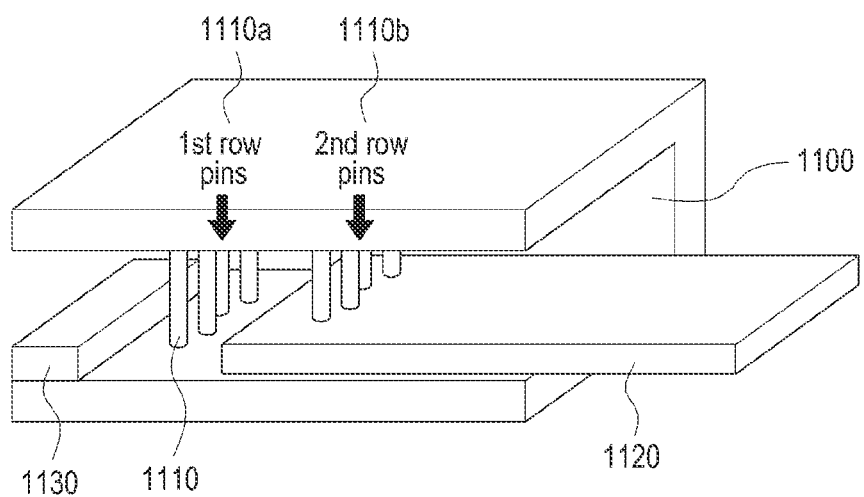
Figure 11C:
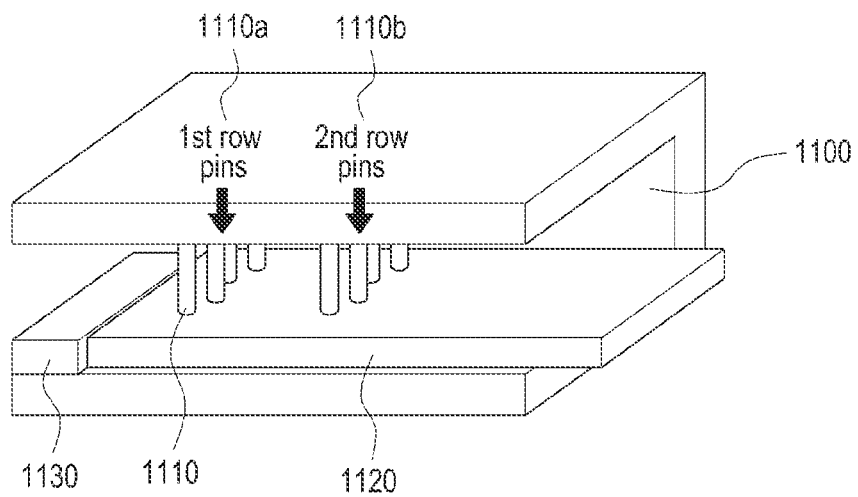

FIGS. 11A, 11B, and 11C illustrate a process of inserting a strip into a strip connector according to an embodiment of the present invention. Referring to FIGS. 11A to 11C, when a strip 1120 is inserted into a receiving part 1100 of a strip connector, a plurality of pins 1110 disposed in the strip connector contact the strip.

In addition, the plurality of pins 1110 are configured to be moved upward by a resilient member (not illustrated) as illustrated when the strip 1120 is inserted into the receiving part 1100. For example, referring to FIG. 11B, when the strip 1120 is inserted to an intermediate position, the pins 1110b disposed in the second column may be moved upward. When the pins 1110b disposed in the second column are detected to be moved upward, the blood glucose measuring device determines that the strip 1120 is inserted to the intermediate position. Furthermore, for example, referring to FIG. 11C, when the strip 1120 is inserted to the end position of the strip receiving part to contact a stopper 1130, the pins 1110a disposed in the first column as well as the pins 1110b disposed in the second column may be moved upward. When the blood glucose measuring device detects that the pins 1110a disposed in the first column are moved upward, the blood glucose measuring device detects that the strip 1120 is completely inserted to the strip receiving part.

According to an embodiment of the present invention, the pins 1110a and 1110b may be implemented in the form of a pogo pin or a C-clip to move upward during the insertion of the strip 1120.

Figure 12:
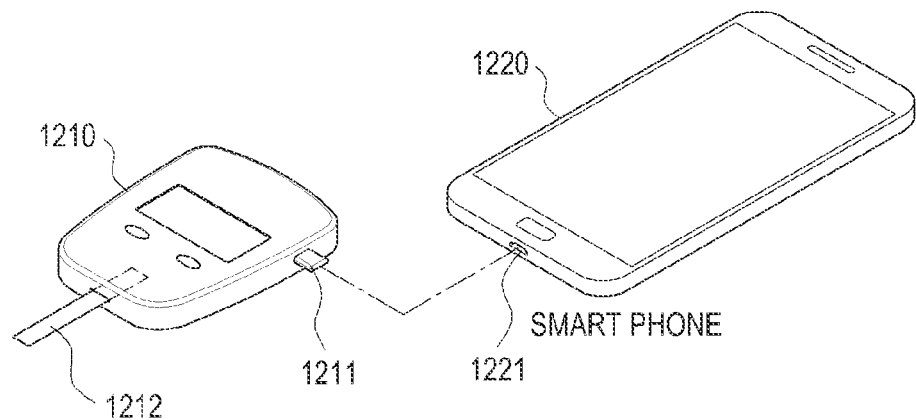
FIG. 12 is a diagram illustrating a connection between a blood glucose measuring device and an electronic device according to an embodiment of the present invention.

FIG. 12 illustrates a connection between a blood glucose measuring device and an electronic device according to an embodiment of the present invention.

Referring to FIG. 12, according to an embodiment of the present invention, a blood glucose measuring device 1210 may be directly connected to an electronic device 1220 (e.g., a smart phone) through connectors 1211 and 1221. The connector 1221 of the electronic device 1220 may perform a function for data communication or charging in the electronic device 1220.

In addition, although not illustrated in FIG. 12, the blood glucose measuring device 1210 may also be connected to the electronic device 1220 through an earphone jack connector of the electronic device 1220. Furthermore, although not illustrated in FIG. 12, the blood glucose measuring device 1210 may also be wirelessly connected to the electronic device 1220 through short range wireless communication (e.g., Bluetooth).

According to an embodiment of the present invention, when the electronic device 1220 is connected while a strip 1212 is inserted into the blood glucose measuring device 1210, the blood glucose measuring device 1210 measures blood glucose with power supplied to the blood glucose measuring device 1210. The measured blood glucose data may be transmitted from the blood glucose measuring device 1210 to the electronic device 1220.

In addition, the electronic device 1220, when the blood glucose measuring device 1210 is connected thereto, may identify that the connected device is the blood glucose measuring device 1210 and automatically execute an application related to management of blood glucose.

Figure 13:
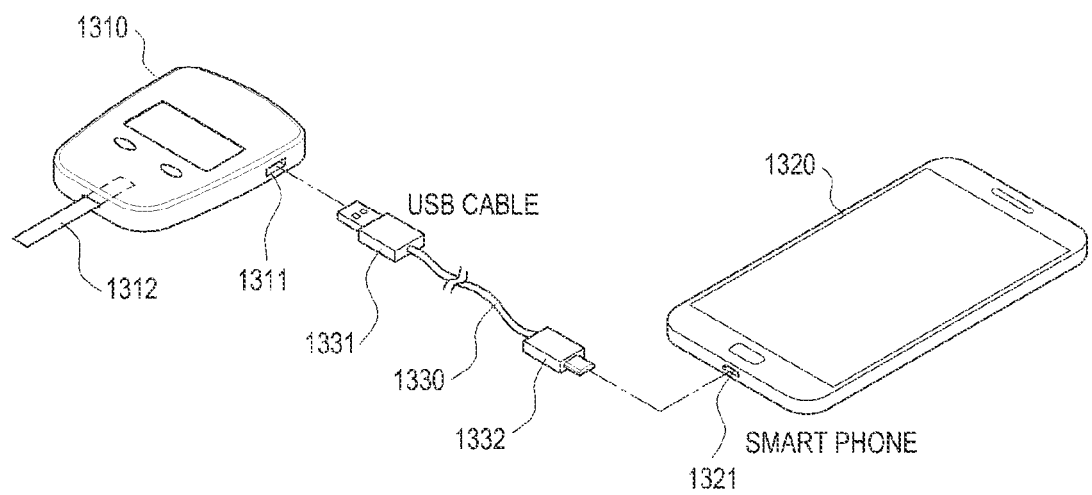
FIG. 13 is a diagram illustrating a connection between a blood glucose measuring device and an electronic device according to an embodiment of the present invention.

FIG. 13 is a diagram illustrating a connection between a blood glucose measuring device and an electronic device according to an embodiment of the present invention.

Referring to FIG. 13, according to an embodiment of the present invention, a blood glucose measuring device 1310 may be connected to an electronic device 1320 (e.g., a smart phone) through a cable 1330 (e.g., a USB cable) connected to connectors 1311 and 1321. For example, one end 1331 of the USB cable 1330 is connected to the connector 1311 of the blood glucose measuring device 1310, and an opposite end 1332 of the USB cable 1330 is connected to the connector 1321 of the electronic device 1320, thereby enabling communication between the devices. The connector 1321 of the electronic device 1320 may perform a data communication function or a charging function in the electronic device 1320.

According to an embodiment of the present invention, the above-described blood glucose measuring device may be manufactured in a module form and then mounted within an electronic device when or after the electronic device is manufactured. In addition, according to an embodiment of the present disclosure, the blood glucose measuring device may also be mounted in a module form within a device (e.g., a smart phone casing or a battery casing) that may be mounted to an electronic device and electrically connected to the electronic device.

Figure 14:
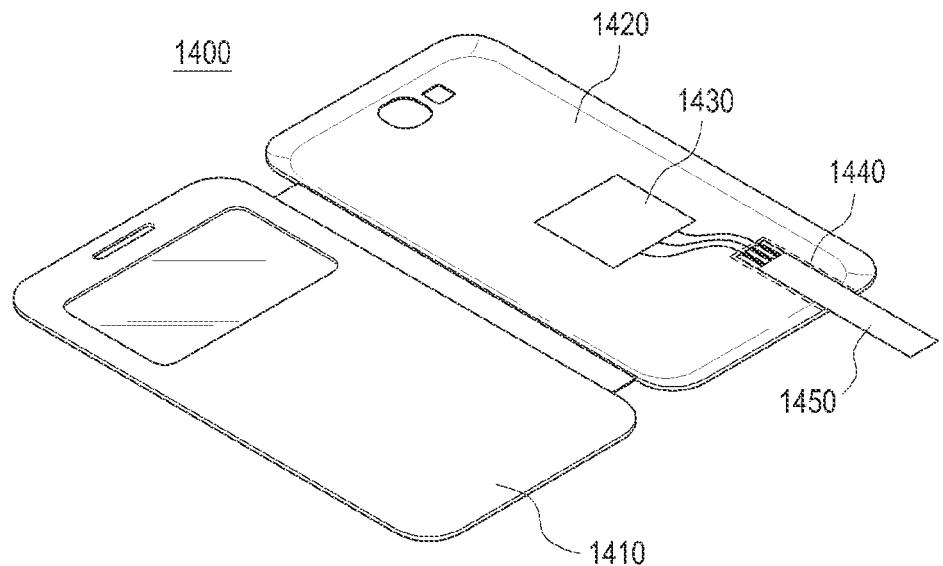
FIG. 14 is a diagram illustrating an electronic device casing including a blood glucose measuring module according to an embodiment of the present invention.

FIG. 14 is a diagram illustrating an electronic device casing including a blood glucose measuring module according to various an embodiment of the present invention.

Referring to FIG. 14, a blood glucose measuring module 1430 may be mounted to a casing 1400 of an electronic device.

The casing 1400 includes a front cover 1410 and a rear cover 1420. According to another embodiment of the present invention, the casing 1400 may include only one of the front or rear cover 1410 and 1420.

The blood glucose measuring module 1430 may be mounted to, attached to, or embedded in the front or rear cover 1410 or 1420 of the casing 1400.

The front or rear cover 1410 or 1420 of the casing 1400 includes, on a side thereof, a strip receiving part 1440 into which a strip 1450 is inserted. The strip receiving part 1440 includes a plurality of pins formed therein as described above. The plurality of pins is electrically connected to the blood glucose measuring module 1430.

When the strip 1450 is inserted into the strip receiving part 1440, the electrode pattern of the inserted strip 1450 is detected through the plurality of pins as described above, and the type of the strip is determined accordingly.

The casing 1400 may be coupled to an electronic device (e.g., a smart phone). When the casing 1400 is coupled to the electronic device, the blood glucose measuring module 1430 may be electrically connected to a main body of the electronic device through a wired/wireless communication unit to communicate with the electronic device. In addition, according to an embodiment of the present invention, the blood glucose measuring module 1430 also communicates with the main body of the electronic device through a Near Field Communication (NFC) communication scheme.

According to various an embodiment of the present invention, a user may replace only the casing 1400 of the electronic device with a blood glucose measuring device, thereby achieving the same effect as including a blood glucose measuring device within the electronic device itself. In addition, according to an embodiment of the present invention, various different types of strips may be identified, and the user is therefore able to measure blood glucose by coupling the casing 1400 to his/her own electronic device regardless of the manufacturer of the sensor strip or the specific product used as the sensor strip.

Furthermore, the blood glucose data measured through the blood glucose measuring module 1430 of the casing 1400 may be transmitted to and managed in the electronic device in real time.

Figure 15:
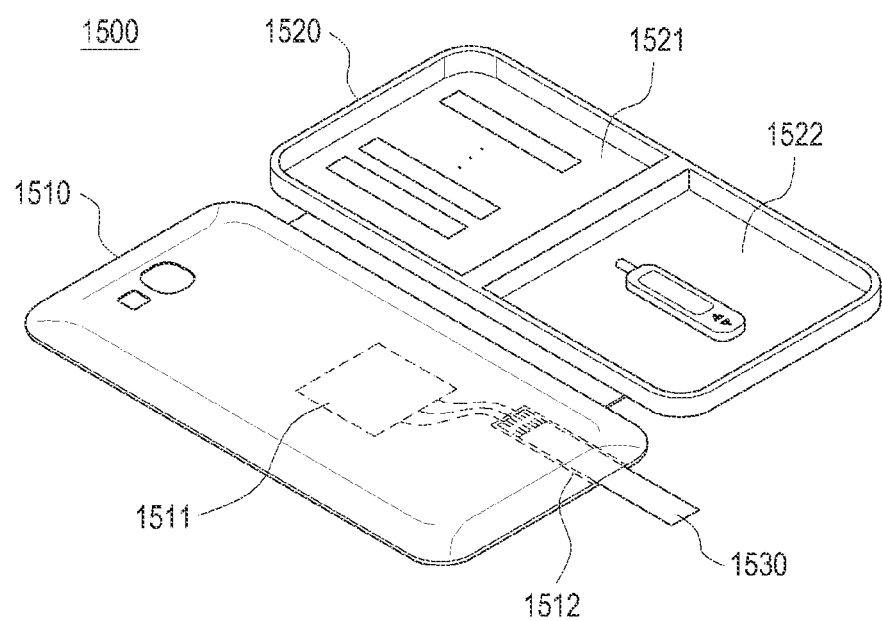
FIG. 15 is a diagram illustrating a battery cover including a blood glucose measuring module according to an embodiment of the present invention.

FIG. 15 is a diagram illustrating a battery cover including a blood glucose measuring module according to an embodiment of the present invention.

Referring to FIG. 15, a casing 1500 of an electronic device according to an embodiment of the present invention includes a first rear cover 1510 and a second rear cover 1520.

The first rear cover 1510 is coupled to the rear surface of the electronic device and includes a blood glucose measuring module 1511. When the first rear cover 1510 is coupled to the rear surface of the electronic device, the blood glucose measuring module 1511 is electrically connected to a main body of the electronic device through a wired/wireless communication unit to communicate with the electronic device. In addition, according to an embodiment of the present invention, the blood glucose measuring module 1511 may also communicate with the main body of the electronic device through a Near Field Communication (NFC) communication scheme.

The first rear cover 1510 includes, on a side thereof, a strip receiving part 1512 into which a strip 1530 is inserted, and the strip receiving part 1512 includes a plurality of pins formed therein as described above. The plurality of pins is electrically connected to the blood glucose measuring module 1511.

When the strip 1530 is inserted into the strip receiving part 1512, the electrode pattern of the inserted strip 1530 is detected through the plurality of pins as described above, and the type of the strip is determined accordingly.

The second rear cover 1520 is configured to be connected to or separated from the first rear cover 1510. Furthermore, the second rear cover 1520 is coupled to the first rear cover 1510. When the second rear cover 1520 is coupled to the first rear cover 1510, an internal space may be formed between the first and second rear covers 1510 and 1520. A strip storage section 1521 and a blood collection needle storage section 1522 are formed in the formed internal space. Accordingly, a user can store and hold, in the casing 1500, a strip or a blood collection needle necessary for blood glucose measurement without separately bringing the strip or the blood collection needle.

A casing of an electronic device, according to an embodiment of the present invention, may include a strip receiving part having a plurality of pins therein, the pins being arranged in such a manner that at least one of the pins contacts at least one electrode formed in a strip for blood glucose measurement when the strip is inserted into the strip receiving part; a blood glucose measuring module that identifies the type of strip for blood glucose measurement which is inserted into the strip receiving part and makes a control to apply a voltage configured in response to the identified type of strip to each pin of the strip receiving part; and a communication unit that transmits blood glucose related information measured through the blood glucose measuring module to the electronic device when the casing is coupled to the electronic device.

According to an embodiment of the present invention, the casing may further include a first rear cover that is coupled to the rear surface of the electronic device and provided with the blood glucose measuring module; and a second rear cover that is coupled to the first rear cover and has a storage section formed in a space which the first and second rear covers form when being coupled to each other, wherein the storage section accommodates a tool related to measuring blood glucose.

Figure 16A:
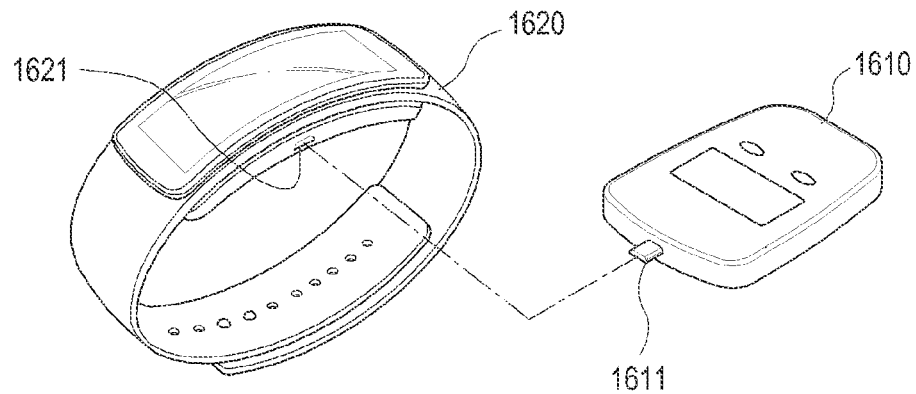
FIGS. 16A and 16B are diagrams illustrating a connection between a blood glucose measuring device and a wearable device according to an embodiment of the present invention.
Figure 16B:
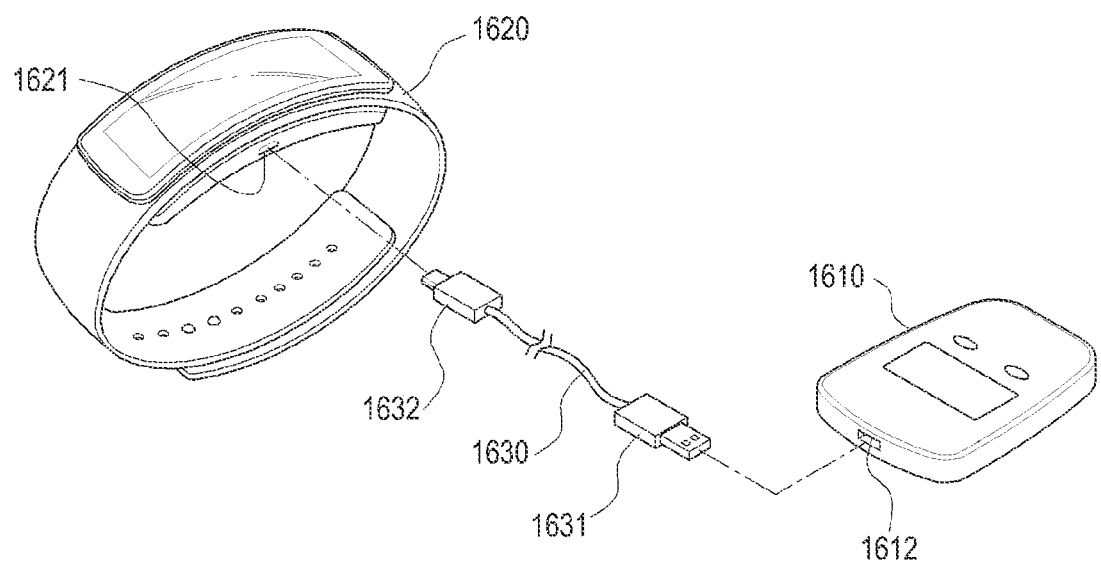

FIGS. 16A and 16B are diagrams illustrating a connection between a blood glucose measuring device and a wearable device according to an embodiment of the present invention.

Referring to FIG. 16A, according to an embodiment of the present invention, a blood glucose measuring device 1610 may be directly connected to a wearable device 1620 (e.g., a watch type device or a glasses type device) through connectors 1611 and 1621. The connector 1621 of the wearable device 1620 may perform a function for data communication or charging in the wearable device 1620.

In addition, although not illustrated in FIG. 16A, the blood glucose measuring device 1610 may also be connected to the wearable device 1620 through an earphone jack connector of the wearable device 1220. Furthermore, although not illustrated in FIG. 16A, the blood glucose measuring device 1610 may also be wirelessly connected to the wearable device 1620 through short range wireless communication (e.g., Bluetooth).

According to an embodiment of the present invention, when the wearable device 1620 is connected while a strip is inserted into the blood glucose measuring device 1610, the blood glucose measuring device 1610 measures blood glucose with power supplied to the blood glucose measuring device 610. The measured blood glucose data is transmitted from the blood glucose measuring device 1610 to the wearable device 1620.

In addition, the wearable device 1620, when the blood glucose measuring device 1610 is connected thereto, identifies that the connected device is the blood glucose measuring device 1610 and automatically executes an application related to management of blood glucose.

FIG. 16B is a diagram illustrating a connection between a blood glucose measuring device and a wearable device according to an embodiment of the present invention.

Referring to FIG. 16B, according to an embodiment of the present invention, a blood glucose measuring device 1610 is connected to a wearable device 1620 (e.g., a watch type device) through a cable 1630 (e.g., a USB cable) connected to connectors 1612 and 1621. For example, one end 1631 of the USB cable 1630 is connected to the connector 1612 of the blood glucose measuring device 1610, and an opposite end 1632 of the USB cable 1630 is connected to the connector 1621 of the wearable device 1620, whereby communication between the devices is possible. The connector 1621 of the wearable device 1620 may perform a function for data communication or charging in the wearable device 1620.

According to an embodiment of the present invention, the above-described blood glucose measuring device may be manufactured in a module form and then mounted within a wearable device during or after manufacture of the wearable device. According to an embodiment of the present invention, the blood glucose measuring device may also be included in a module form in a separate device electrically connected to the wearable device.

Figure 17:
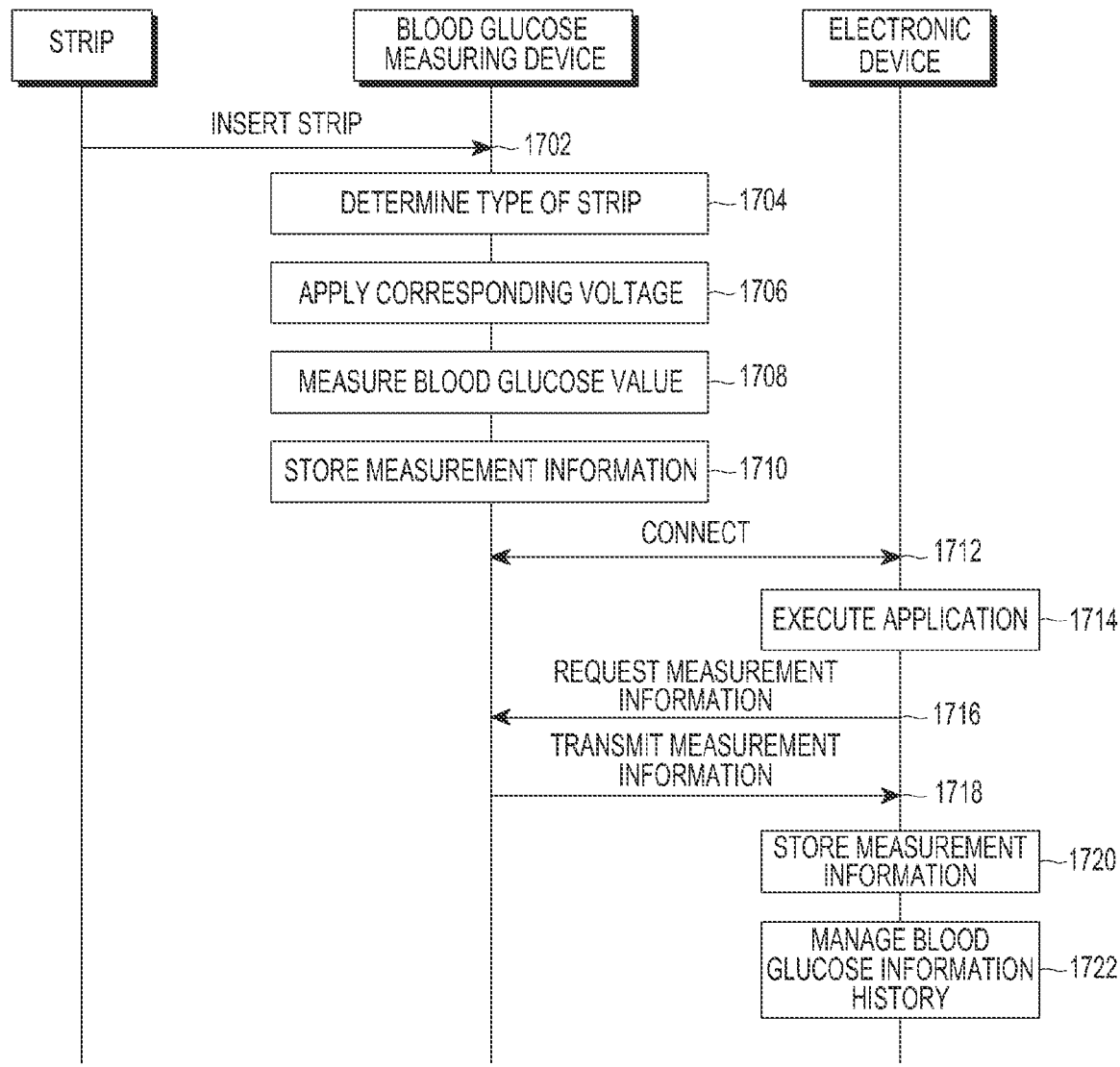
FIG. 17 is a signal flow diagram illustrating a communication procedure between a blood glucose measuring device and an electronic device according to an embodiment of the present invention.

FIG. 17 is a signal flow diagram illustrating a communication procedure between a blood glucose measuring device and an electronic device according to an embodiment of the present invention. Referring to FIG. 17, when a strip is inserted into a strip receiving part of the blood glucose measuring device in step 1702, the blood glucose measuring device determines the type of the strip in step 1704. The corresponding voltage is applied to each pin of the strip receiving part in step 1706, and a blood glucose value is measured, in step 1708. The measure blood glucose value is stored in step 1710.

When the blood glucose measuring device is connected to the electronic device through a wired/wireless communication unit in step 1712, a related application is automatically executed by the electronic device, in step 1714. Upon the execution of the application, the electronic device requests the measurement information from the blood glucose measuring device in operation 1716. The blood glucose measuring device transmits the measured information to the electronic device in response to the request, in step 1718.

The electronic device stores the received measurement information in step 1720 and analyzes the stored measurement information to manage history for the blood glucose related information in step 1722.

Figure 18:
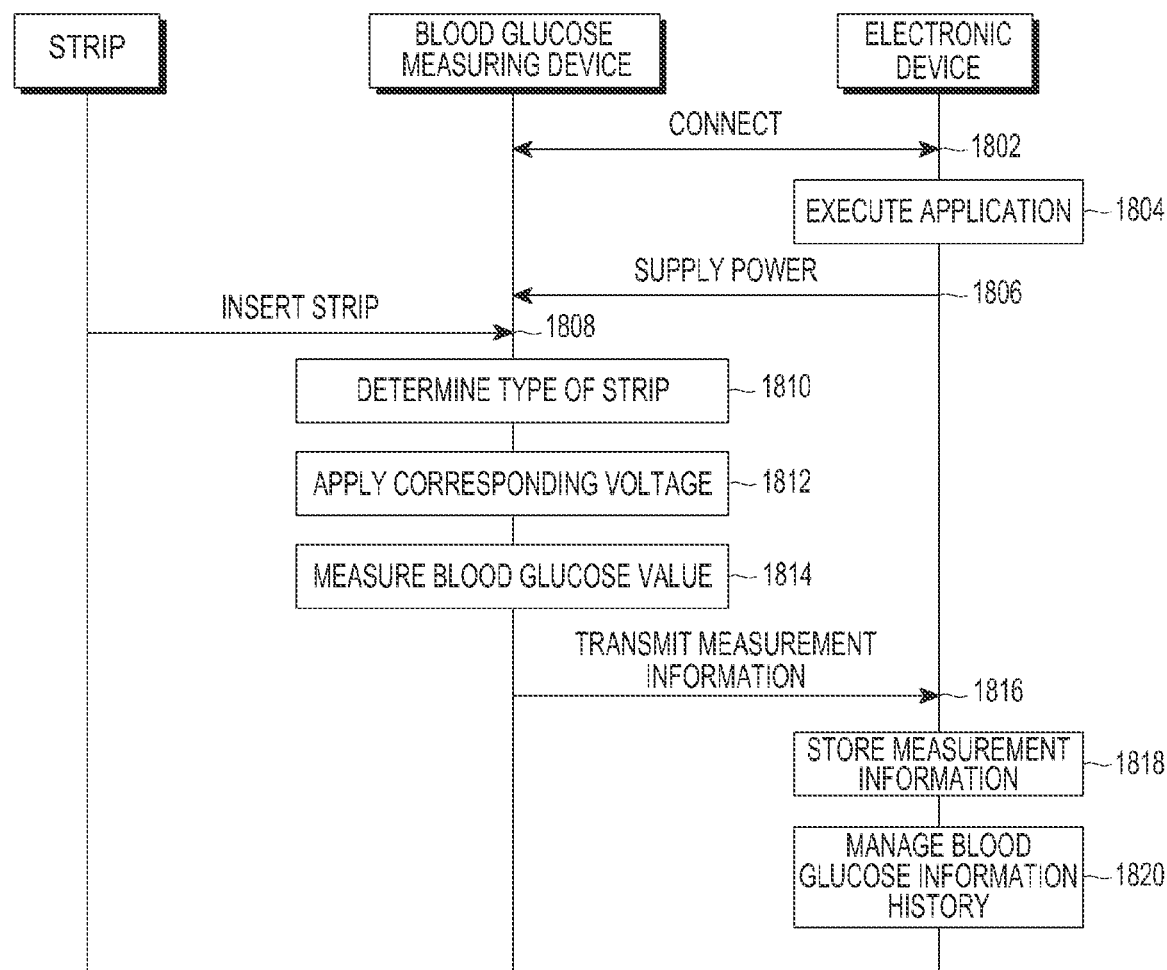
FIG. 18 is a signal flow diagram illustrating a communication procedure between a blood glucose measuring device and an electronic device according to an embodiment of the present invention.

FIG. 18 is a signal flow diagram illustrating a communication procedure between a blood glucose measuring device and an electronic device according to an embodiment of the present invention.

Referring to FIG. 18, when the blood glucose measuring device is connected to the electronic device through a wired/wireless communication unit in step 1802, a related application is automatically executed in the electronic device, in step 1804.

In step 1806, power is supplied from the electronic device to the connected blood glucose measuring device.

When a strip is inserted into a strip receiving part of the blood glucose measuring device in step 1808, the type of the strip is determined, in step 1810. The corresponding voltage is applied to each pin of the strip receiving part in step 1812, and a blood glucose value is measured in step 1814. The measured blood glucose value may be stored or directly transmitted to the connected electronic device without being stored.

The electronic device stores the received measurement information in step 1818, and analyzes the stored measurement information to manage history for the blood glucose related information, in step 1820.

Figure 19:
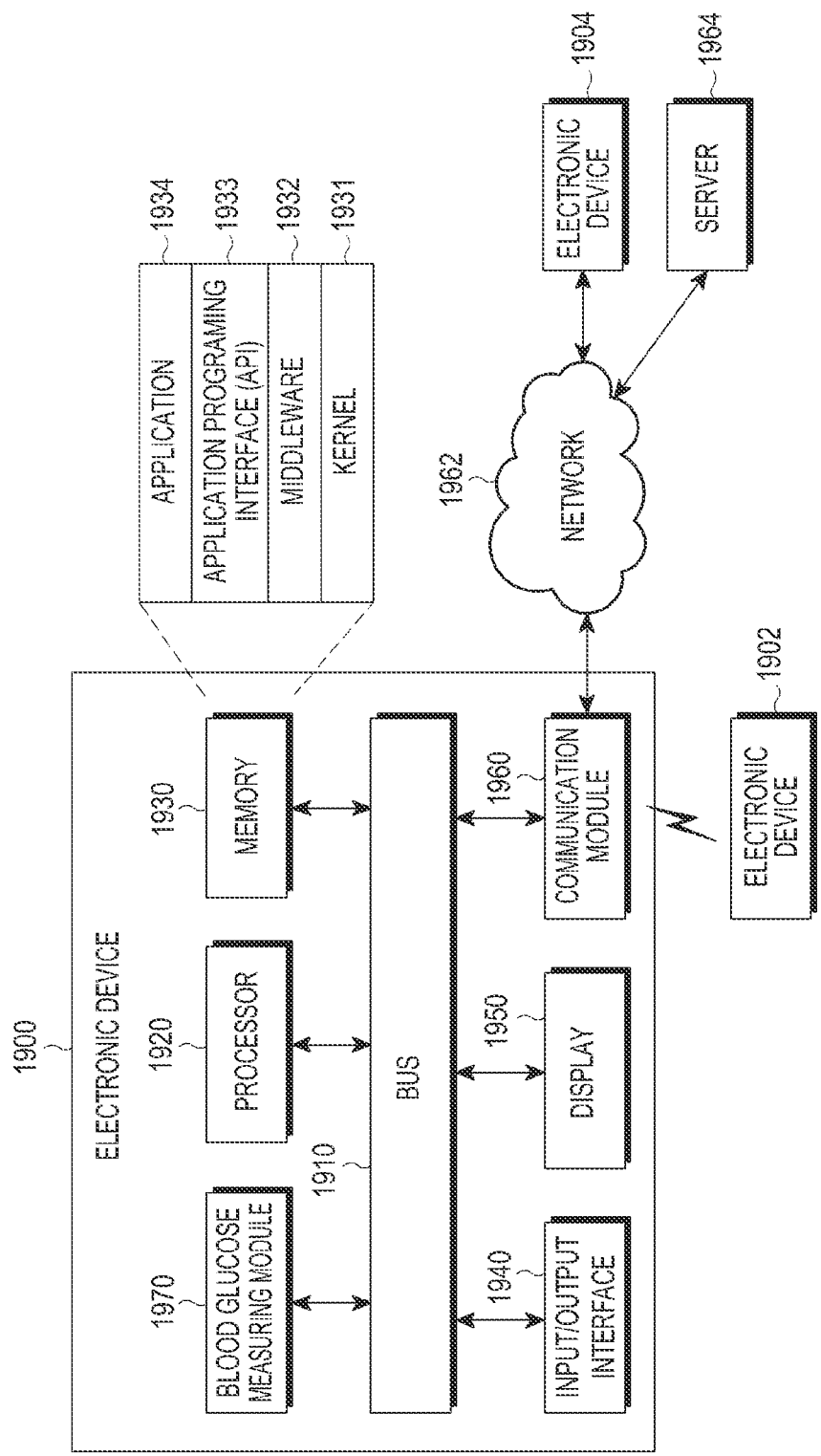
FIG. 19 is a diagram illustrating a network environment according to an embodiment of the present invention.

FIG. 19 is a diagram illustrating a network environment 1900 including an electronic device 1901 according to an embodiment of the present invention. Referring to FIG. 19, the electronic device 1901 includes a bus 1910, a processor 1920, a memory 1930, an input/output interface 1940, a display 1950, a communication interface 1960, and a blood glucose measuring module 1970.

The bus 1910 is a circuit that interconnects the above-described elements and transfers communications (e.g., control messages) between the above-described elements.

The processor 1920 receives instructions from the other elements (e.g., the memory 1930, the input/output interface 1940, the display 1950, the communication interface 1960, or the blood glucose measuring module 1970) through the bus 1910, decodes the received instructions, and performs calculation or data processing according to the decoded instructions.

The memory 1930 stores instructions or data received from or generated by the processor 1920 or the other elements (e.g., the input/output interface 1940, the display 1950, the communication interface 1960, or the blood glucose measuring module 1970). The memory 1930 includes programming modules, for example, a kernel 1931, middleware 1932, an Application Programming Interface (API) 1933, applications 1934, and the like. The aforementioned programming modules may be configured with software, firmware, hardware, or a combination of two or more thereof.

The kernel 1931 control or manages system resources (e.g., the bus 1910, the processor 1920, the memory 1930, or the like) that are used in performing operations or functions implemented in the other programming modules, for example, the middleware 1932, the API 1933, and the applications 1934. In addition, the kernel 1931 provides an interface through which the middleware 1932, the API 1933, and the applications 1934 are able to access individual elements of the electronic device 1901 to control or manage the same.

The middleware 1932 functions as a relay that allows the API 1933 or the applications 1934 to communicate with the kernel 1931 to exchange data. Furthermore, in regard to task requests received from the applications 1934, the middleware 1932 controls (e.g., scheduling or load balancing) task requests, using a method such as assigning, to at least one of the applications 1934, a priority for using the system resources (e.g., the bus 1910, the processor 1920, and the memory 1930) of the electronic device 1901.

The API 1933 is an interface through which the applications 1934 control functions provided from the kernel 1931 or the middleware 1932, and may include, for example, an interface or function (e.g., instruction) for file control, window control, image processing, text control, or the like.

According to an embodiment of the present invention, the applications 1934 may include, for example, a Short Message Service (SMS)/Multimedia Messaging Service (MMS) application, an email application, a calendar application, an alarm application, a health care application (e.g., application for measuring a quantity of exercise or blood sugar) or an environment information application (e.g., application providing information associated with pressure, humidity or temperature). Additionally or alternatively, the applications 1934 may include an application related to an information exchange between the electronic device 1901 and an external electronic device (e.g., an electronic device 1904). The application related to the information exchange may include, for example, a notification relay application for transferring predetermined information to the external electronic device or a device management application for managing the external electronic device.

For example, the notification relay application may include a function of transferring notification information generated by another application (e.g., the SMS/MMS application, the email application, the health care application or the environment information application) of the electronic device 1901 to the external electronic device (e.g., the electronic device 1904). Additionally or alternatively, the notification relay application may, for example, receive notification information from an external electronic device (e.g., the electronic device 1904) and provide the same to a user. The device management application may, for example, manage (e.g., install, delete, or update) a function for at least a part of the external electronic device (e.g., the electronic device 1904) communicating with the electronic device 1901 (e.g., turning on/off the external electronic device itself (or some elements thereof) or adjusting the brightness (or resolution) of a display), applications operating in the external electronic device, or services provided from the external electronic device (e.g., a telephone call service or a message service).

According to an embodiment of the present invention, the applications 1934 may include an application designated according to an attribute (e.g., the type of the electronic device) of the external electronic device (e.g., the electronic device 1904). For example, when the external electronic device is a Motion Picture Experts Group (MPEG) Audio-Layer 3 (MP3) player, the applications 1934 may include an application related to the reproduction of music. Similarly, when the external electronic device is a mobile medical device, the applications 1934 include an application related to the health care. According to an embodiment of the present invention, the applications 1934 may include an application designated to the electronic device 1901 and/or an application received from an external electronic device (e.g., a server 1964 or the electronic device 1904). In addition, the applications 1934 may include an application related to blood glucose measurement, and execute various types of operations in conjunction with the blood glucose measuring module 1970.

The input/output interface 1940 transfers instructions or data, which are input by a user through an input/output device (e.g., a sensor, a keyboards, or a touch screen), for example, through the bus 1910 to the processor 1920, the memory 1930, the communication interface 1960, or the blood glucose measuring module 1970. For example, the input/output interface 1940 may provide, to the processor 1920, data for a user's touch input through the touch screen. The input/output interface 1940 may output, through the input/output device (e.g., a speaker or a display), instructions or data received through the bus 1910 from the processor 1920, the memory 1930, the communication interface 1960, or the blood glucose measuring module 1970. For example, the input/output interface 1940 may output voice data processed by the processor 1920 to the user through the speaker.

The display 1950 displays various types of information (e.g., multimedia data or text data) to the user. In addition, according to an embodiment of the present invention, through various methods, the display 1950 may display an input pad through which various characters, numbers, and symbols may be input to an input window on a screen.

The communication interface 1960 connects communications between the electronic device 1901 and the external device (e.g., the electronic device 1904 or the server 1964). For example, the communication interface 1960 may communicate with the external electronic device while being connected to a network 1962 through wireless or wired communication. The wireless communication may include, for example, Wireless Fidelity (Wi-Fi), BlueTooth (BT), Near Field Communication (NFC), Global Positioning System (GPS) and/or cellular communication (e.g., Long Term Evolution (LTE), LTE-Advanced (LTE-A), Code Division Multiple Access (CDMA), Wideband CDMA (WCDMA), Universal Mobile Telecommunications System (UMTS), Wireless Broadband (WiBro), Global System for Mobile communications (GSM), or the like). The wired communication may include at least one of, for example, a Universal Serial Bus (USB), a High Definition Multimedia Interface (HDMI), Recommended Standard 232 (RS-232), and a Plain Old Telephone Service (POTS).

According to an embodiment of the present invention, the network 1962 may be a communication network. The communication network may include any of a computer network, the Internet, the Internet of things, and/or a telephone network. According to an embodiment of the present invention, a protocol (e.g., a transport layer protocol, a data link layer protocol, or a physical layer protocol) for the communication between the electronic device 1901 and the external device may be supported by at least one of the applications 1934, the application programming interface 1933, the middleware 1932, the kernel 1931, and the communication interface 1960.

Although FIG. 19 depicts the electronic device 1901 as including the communication interface 1960 and communicates with the external electronic device 1904 or the server 1964 through the network 1962, the electronic device 1901 may be implemented to independently operate therein without a separate communication function, in accordance with embodiments of the present invention.

According to an embodiment of the present invention, the server 1964 may support the operation of the electronic device 1901 by performing at least one of the operations (or functions) performed by the electronic device 1901. For example, the server 1964 may include a blood glucose measurement processing server module (not illustrated) that supports the blood glucose measuring module 1970 implemented in the electronic device 1901. For example, the blood glucose measurement server module may include at least one element of the blood glucose measuring module 1970 to perform at least one of the operations (or functions) carried out by the blood glucose measuring module 1970 or act on behalf of the blood glucose measuring module 1970.

The blood glucose measuring module 1970 processes at least some of information obtained from the other elements (e.g., the processor 1920, the memory 1930, the input/output interface 1940, or the communication interface 1960) and provides the processed information to the user in various manners.

Although the blood glucose measuring module 1970 is illustrated as a separate module from the processor 120 in FIG. 19, at least a part of the blood glucose measuring module 1970 may be included in the processor 1920 or the display 1950, and all the functions of the blood glucose measuring module 1970 may be implemented in the illustrated processor 1920 or another processor, in accordance with embodiments of the present invention.

Figure 20:
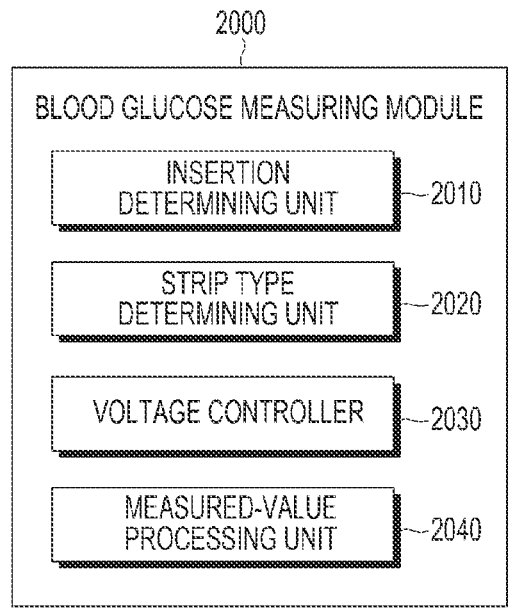
FIG. 20 is a block diagram illustrating a detailed structure of a blood glucose measuring module according to an embodiment of the present invention.

FIG. 20 is a block diagram illustrating a detailed structure of a blood glucose measuring module according to an embodiment of the present invention.

Referring to FIG. 20, the blood glucose measuring module according to an embodiment of the present invention includes an insertion determining unit 2010, a strip type determining unit 2020, a voltage controller 2030, and a measured-value processing unit 2040.

When a strip is inserted through a strip connector of the blood glucose measuring module, the insertion determining unit 2010 determines whether the strip is inserted. At this time, the insertion determining unit 2010 may also determine a degree of insertion of the strip (e.g., may determine whether the strip is partially or completely inserted).

When insertion determining unit 2010 determines that the strip is completely inserted, the insertion determining unit 2010 supplies power to the strip connector in order to determine the type of the strip. The strip type determining unit 2020 checks a voltage and/or current detected from each pin of the strip connector and identifies the pattern of the inserted strip with reference to pre-stored strip information. In addition, when a plurality of types of strips have the same pattern, the strip type determining unit 2020 measures the resistance of each pin to identify the type of the strip (e.g., strip makers or model names).

When the type of inserted strip is identified, the voltage controller 2030 identifies the pre-stored strip information. The strip information includes information, such as an electrode type (a dual electrode type or a triple electrode type), an operating voltage, an operating electrode, a counterpart electrode, a standard electrode, and the like, which have been set for each maker or model name.

The voltage controller 2030 checks a voltage to apply to each pin with reference to the identified strip information and controls the power supply unit to apply the voltage corresponding to the identified strip to each pin of the strip connector.

The measured-value processing unit 2040 estimates a blood glucose value, for example, by comparing a voltage of current flowing through each pin of the strip connector with a reference value corresponding to each strip type.

Figure 21:
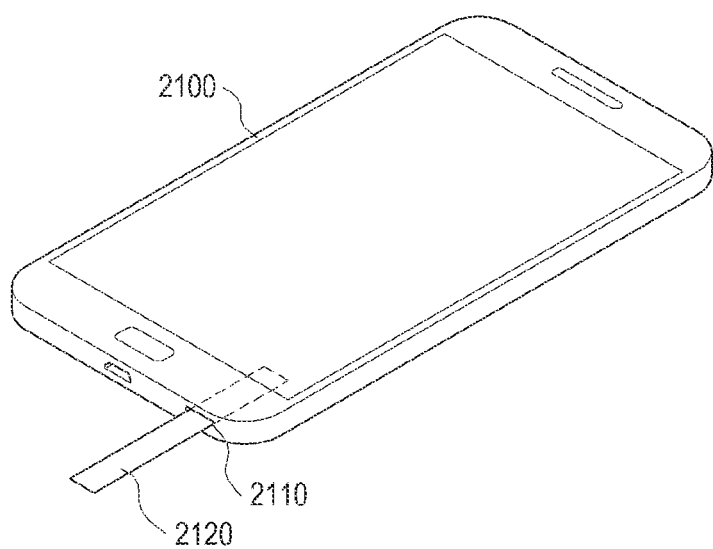
FIG. 21 is a diagram illustrating an electronic device including a blood glucose measuring module according to an embodiment of the present invention.
Figure 22:
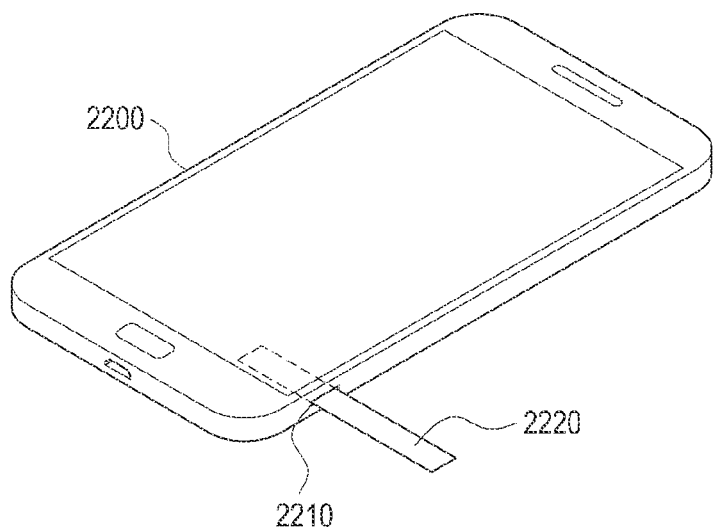
FIG. 22 is a diagram illustrating an electronic device including a blood glucose measuring module according to an embodiment of the present invention.
Figure 23:
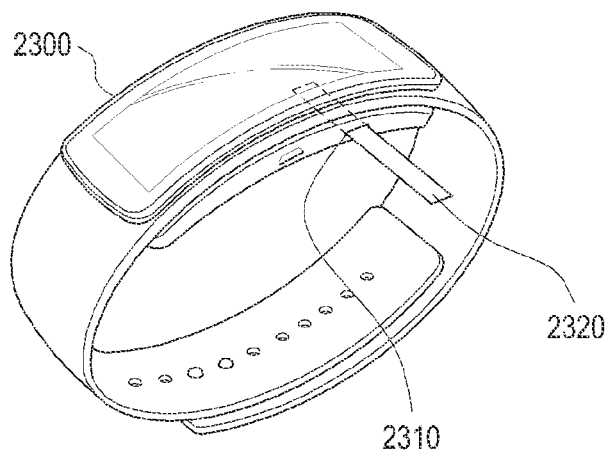
FIG. 23 is a diagram illustrating a wearable device including a blood glucose measuring module according to an embodiment of the present invention.

FIGS. 21, 22, and 23 are diagrams illustrating examples of various types of electronic devices having a blood glucose measuring module therein, according to embodiments of the present invention.

Referring to FIG. 21, an electronic device 2100 includes, on a lower side surface thereof, a strip receiving part 2110 into which a strip 2120 is inserted. Referring to FIG. 22, an electronic device 2200 includes, on a right side surface thereof, a strip receiving part 2210 into which a strip 2220 is inserted. Referring to FIG. 23, an electronic device 2300 includes, on a right side surface thereof, a strip receiving part 2310 into which a strip 2320 is inserted.

Figure 24:
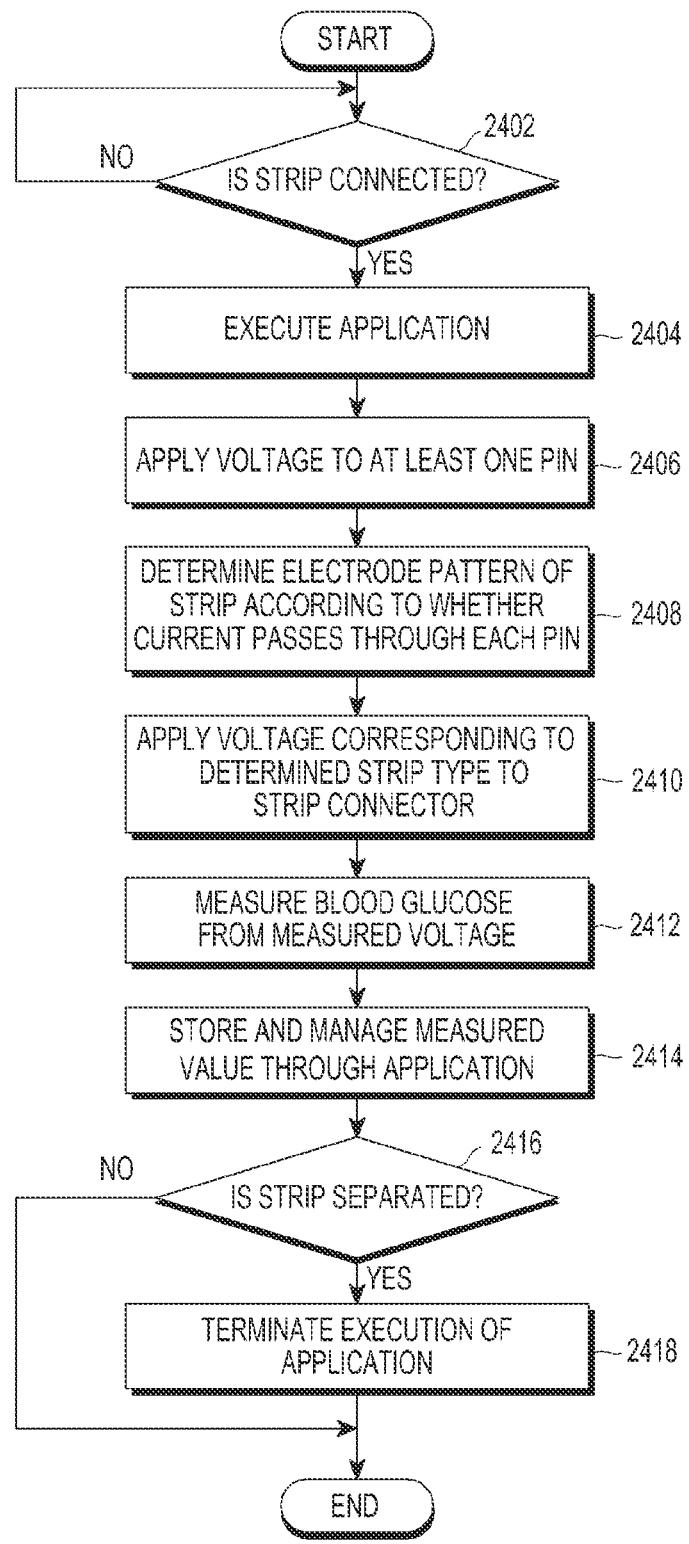
FIG. 24 is a flowchart illustrating a procedure of measuring blood glucose in an electronic device according to an embodiment of the present invention.

FIG. 24 is a flowchart illustrating a procedure of measuring blood glucose in an electronic device according to an embodiment of the present invention. Referring to FIG. 24, when a strip is connected to the electronic device in step 2402, an application (e.g., an application related to management of blood glucose) installed in the electronic device is automatically executed, in step 2404.

According to an embodiment of the present invention, when a voltage is applied to at least one pin, in step 2406, the electrode pattern of the strip is determined according to whether a current passes through each pin, in step 2408.

When a voltage corresponding to the determined strip type is applied to a strip connector of the electronic device, in step 2410, blood glucose is measured from the measured voltage, in step 2412. In step 2414, the measured data may be stored and managed through the application executed in the electronic device.

When the inserted strip is separated in step 2416, execution of the application related to the blood glucose management is automatically terminated, in step 2418.

Figure 25:
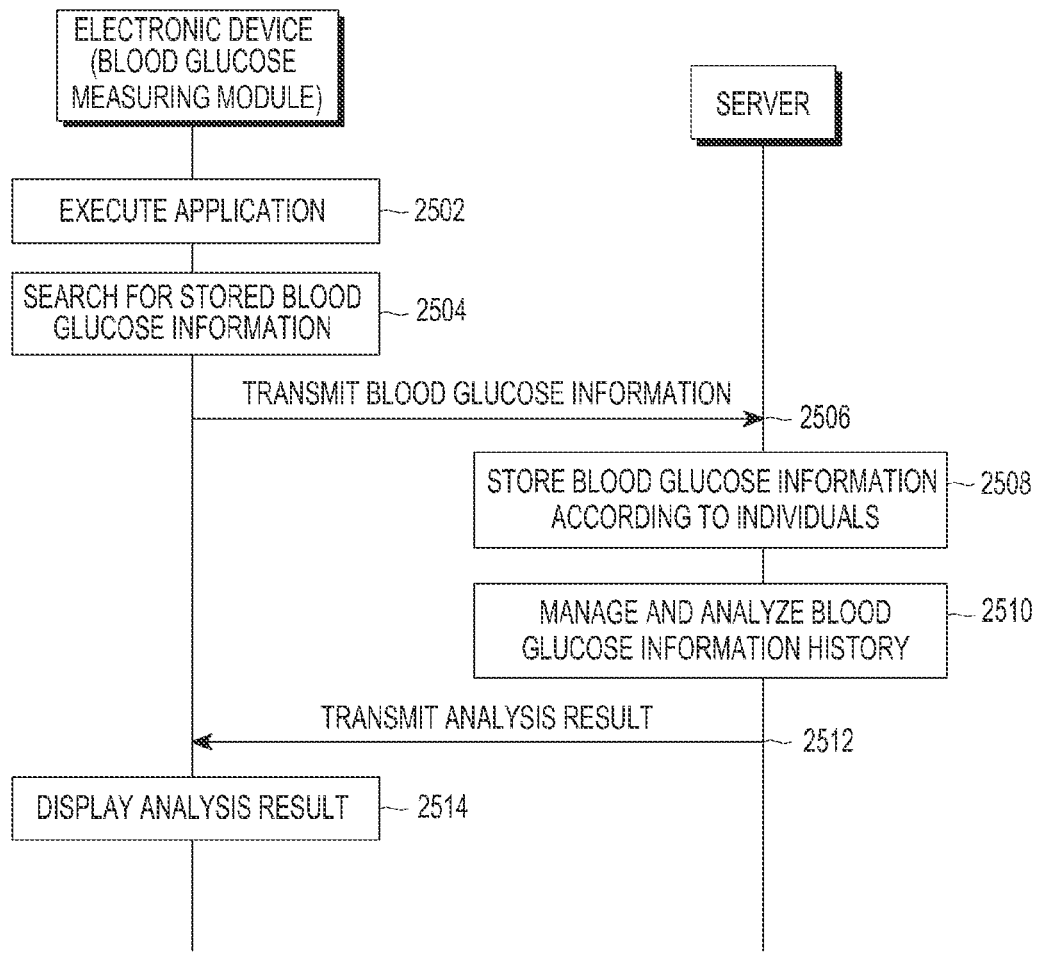
FIG. 25 is a signal flow diagram illustrating a communication procedure between an electronic device and a server according to an embodiment of the present invention.

FIG. 25 is a signal flow diagram illustrating a communication procedure between an electronic device and a server according to an embodiment of the present invention.

Referring to FIG. 25, when the electronic device including a blood glucose measuring module executes an application in step 2502, the electronic device searches a memory for pre-stored blood glucose related information (e.g., measured blood glucose data, dates and times when blood glucose was measured, empty-stomach related information, and the like), in step 2504.

In step 2506, the discovered blood glucose related information is transmitted to the server. In step 2508, the server distinguishes the blood glucose related information received from the electronic device, according to individual users, and stores the received information according to users.

The server manages and analyzes the blood glucose information history in step 2510 and transmits results of the analysis to the electronic device, in step 2512. In step 2514, the electronic device displays the analysis result received from the server on a screen of the electronic device.

Figure 26:
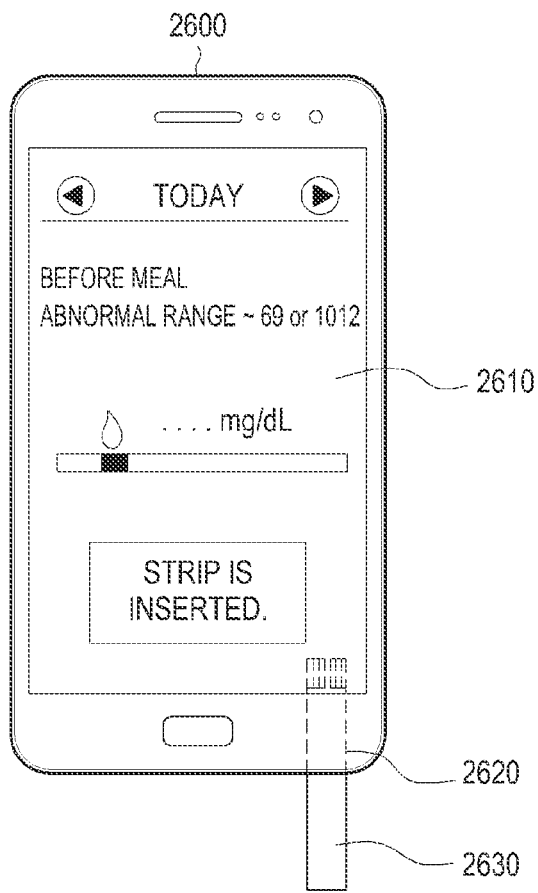
FIG. 26 is a diagram illustrating an example of a blood glucose measurement screen in an electronic device according to an embodiment of the present invention.

FIG. 26 is a diagram illustrating an example of a blood glucose measurement screen in an electronic device according to an embodiment of the present invention. Referring to FIG. 26, when a strip 2630 is inserted into a strip receiving part 2620 in an electronic device 2600, an application related to blood glucose management is automatically executed and displayed on a screen 2610. For example, after the type of the inserted strip 2630 is automatically determined, blood glucose data measured by a blood glucose measuring module is displayed together with a guidance message "Strip is inserted" on the application execution screen 2610 of the electronic device 2600.

Figure 27:
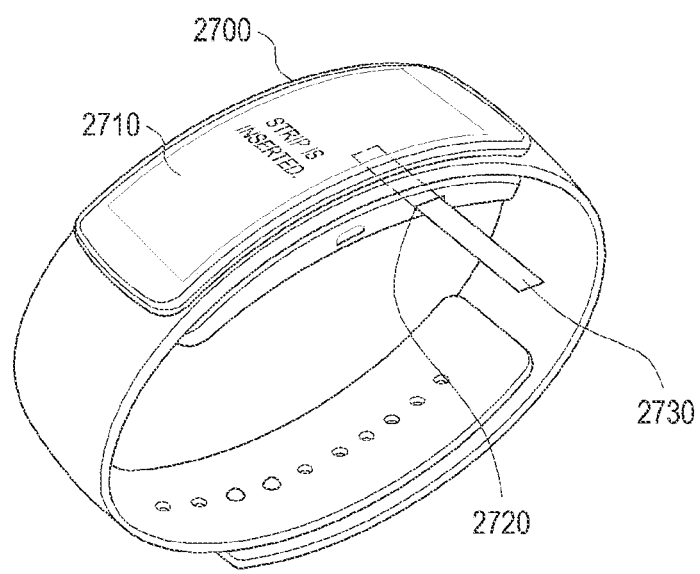
FIG. 27 is a diagram illustrating an example of a blood glucose measurement screen in a wearable device according to an embodiment of the present invention.

FIG. 27 is a diagram illustrating an example of a blood glucose measurement screen in a wearable device according to an embodiment of the present invention. Referring to FIG. 27, when a strip 2730 is inserted into a strip receiving part 2720 in a wearable device 2700, an application related to blood glucose management is automatically executed and displayed on a screen 2710. For example, after the type of the inserted strip 2730 is automatically determined, blood glucose data measured by a blood glucose measuring module is displayed together with a guidance message "Strip is inserted" on the application execution screen 2710 of the wearable device 2700.

Figure 28:
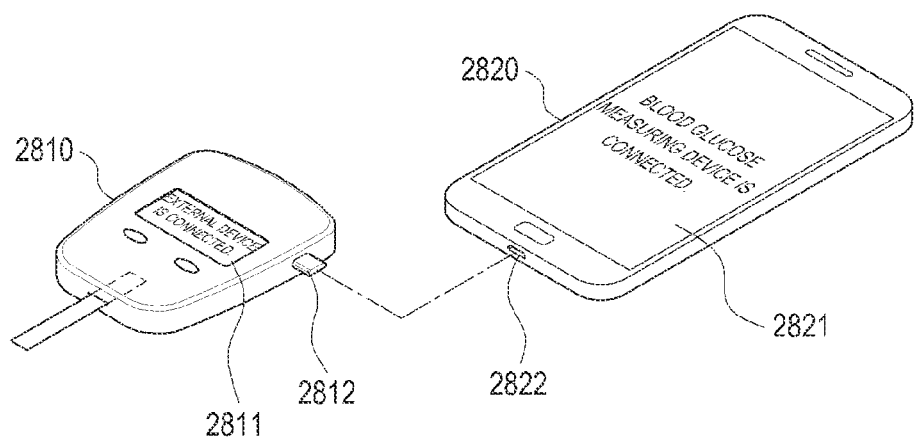
FIG. 28 is a diagram illustrating a connection between a blood glucose measuring device and an electronic device according to an embodiment of the present invention.

FIG. 28 is a diagram illustrating a connection between a blood glucose measuring device and an electronic device according to an embodiment of the present invention. Referring to FIG. 28, when a blood glucose measuring device 2810 and an electronic device 2820 are connected to each other through connectors 2812 and 2822 thereof, while a strip is inserted into the blood glucose measuring device 2810, the connection status is displayed on screens of the respective devices.

For example, a message "External device is connected" is displayed on a screen 2811 of the blood glucose measuring device 2810, and a message "Blood glucose measuring device is connected" is displayed on a screen 2812 of the electronic device 2820.

Figure 29:
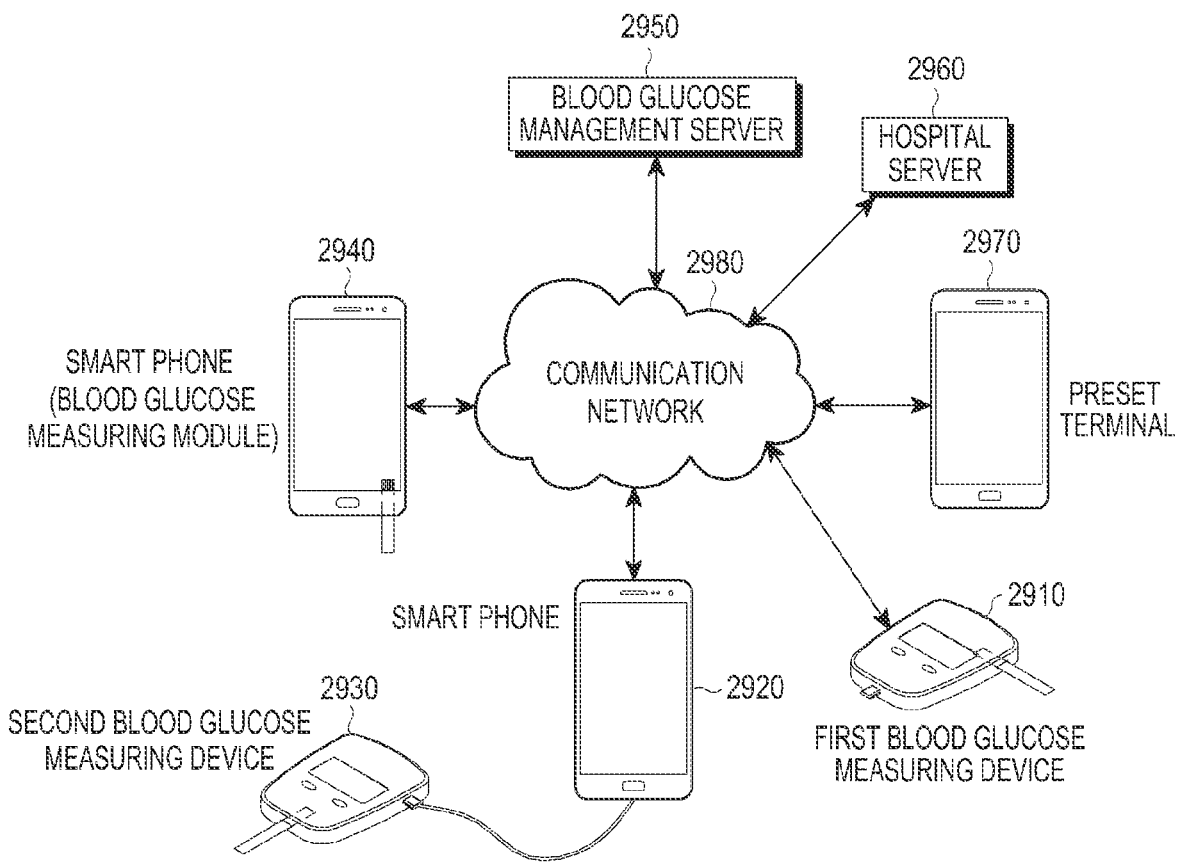
FIG. 29 is a diagram illustrating a network environment according to an embodiment of the present invention.

FIG. 29 is a diagram illustrating a network environment according to an embodiment of the present invention.

Referring to FIG. 29, blood glucose measuring devices or blood glucose measuring modules may be connected in various forms according to an embodiment of the present invention.

For example, a first blood glucose measuring device 2910 may have wired/wireless communication functions therein and may be connected to an external device or a server (e.g., a blood glucose management server 2950 or a hospital server 2960) through a communication network 2980. In addition, a blood glucose measuring device 2930 may be connected to an electronic device (e.g. smart phone 2920) and may be connected to various types of servers (e.g., the blood glucose management server 2950 or the hospital server 2960) or another electronic device (e.g. preset terminal 2970) through the electronic device (e.g. smart phone 2920).

Furthermore, according to an embodiment of the present invention, a blood glucose measuring device may be included in the form of a blood glucose measuring module in an electronic device (e.g. smart phone 2940), and the electronic device may be connected to various types of servers (e.g., the blood glucose management server 2950 or the hospital server 2960) or another electronic device (e.g. preset terminal 2970) through the communication network 2980.

The first and second blood glucose measuring devices 2910 and 2930 or an electronic device having the blood glucose measuring module mounted thereto (e.g., smart phone 2940) may transmit measured blood glucose related data through the communication network 2980 to the various types of servers (e.g., the blood glucose management server 2950 or the hospital server 2960) or another electronic device (e.g. preset terminal 2970).

Accordingly, the blood glucose management server 2950 or the hospital server 2960 may receive and manage the blood glucose related information transmitted from each user's electronic device or blood glucose measuring device. In addition, the hospital server 2960 may analyze the blood glucose related information and transmit the analysis result or emergency information to the corresponding electronic device or blood glucose measuring device.

Furthermore, according to an embodiment of the present invention, when an emergency situation is determined through the analysis of the blood glucose related information, emergency information may be transmitted to the preset terminal 2970, a doctor's preset terminal, or the hospital server 2960.

Figure 30:
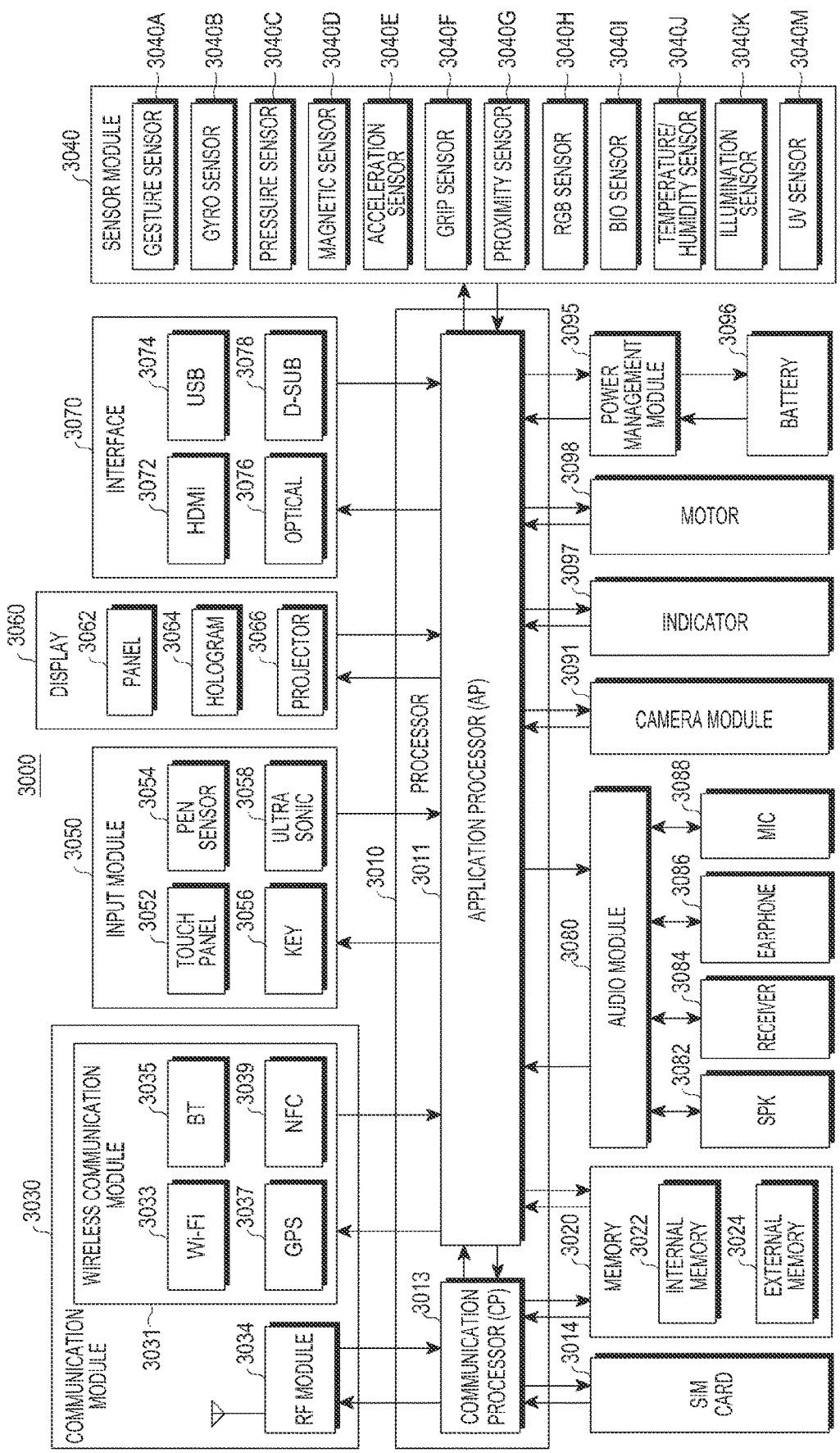
FIG. 30 is a block diagram illustrating a detailed structure of an electronic device according to an embodiment of the present invention.

FIG. 30 is a block diagram illustrating an electronic device according to an embodiment of the present invention. The electronic device 3000 may include, for example, all or a part of the electronic device 1901 illustrated in FIG. 19.

Referring to FIG. 30, the electronic device 3000 includes an Application Processor (AP) 3011, a communication module 3030, a Subscriber Identifier Module (SIM) card 3014, a memory 3020, a sensor module 3040, an input module 3050, a display 3060, an interface 3070, an audio module 3080, a camera module 3091, a power management module 3095, a battery 3096, an indicator 3097, and a motor 3098.

The AP 3011 controls a plurality of hardware or software elements connected thereto by driving an operating system or an application program, process various types of data including multimedia data, and perform calculations. The AP 3011 may be embodied in a System on Chip (SoC). The AP 3011 may further include a graphic processing unit (GPU) (not illustrated).

The communication module 3030 performs data transmission/reception in communication between the electronic device 3000 (e.g., the electronic device 1901) and other electronic devices (e.g., the electronic device 1904 and the server 1964) connected thereto through a network. The communication module 3030 includes a cellular module 3021, a Wi-Fi module 3033, a BlueTooth (BT) module 3035, a GPS module 3037, an NFC module 3039, and a Radio Frequency (RF) module 3034.

The cellular module 3021 provides a voice call, a video call, a message service, or an Internet service through a communication network (e.g., LTE, LTE-A, CDMA, WCDMA, UMTS, WiBro, GSM, or the like). The cellular module 3021 also identifies and authenticates an electronic device in a communication network, for example, using a subscriber identification module (e.g., the SIM card 3014). According to an embodiment of the present invention, the cellular module 3021 may perform at least some of the functions provided by the AP 3011. For example, the cellular module 3021 may perform at least a part of the multimedia control function.

The cellular module 3021 includes a Communication Processor (CP). In addition, the cellular module 3021 may be implemented in the form of a System on Chip (SOC). In FIG. 30, the elements such as the cellular module 3021 (e.g., a communication processor), the memory 3020, the power management module 3095, and the like are illustrated as separate elements from the AP 3011. However, according to an embodiment, the AP 3011 may include at least some of the aforementioned elements (e.g., the cellular module 3021).

The AP 3011 or the cellular module 3021 (e.g., the communication processor) loads, in a volatile memory, instructions or data received from at least one of a non-volatile memory and the other elements connected thereto and process the loaded instructions or data. In addition, the AP 3011 or the cellular module 3021 store, in a non-volatile memory, data received from or generated by at least one of the other elements.

The Wi-Fi module 3033, the BT module 3035, the GPS module 3037, or the NFC module 3039 may include, for example, a processor for processing data transmitted/received through the corresponding module. Although the cellular module 3021, the Wi-Fi module 3033, the BT module 3035, the GPS module 3037, and the NFC module 3039 are illustrated as separate blocks in FIG. 30, at least some (e.g., two or more) of the cellular module 3021, the Wi-Fi module 3033, the BT module 3035, the GPS module 3037, and the NFC module 3039 may be included in one integrated chip (IC) or IC package according to an embodiment. For example, at least some of the processors corresponding to the cellular module 3021, the Wi-Fi module 3033, the BT module 3035, the GPS module 3037, and the NFC module 3039 (e.g., a communication processor corresponding to the cellular module 3021 and a Wi-Fi processor corresponding to the Wi-Fi module 3033) may be implemented as a single SoC.

The RF module 3034 transmits/receives data, for example, an RF signal. Although not illustrated, the RF module 3034 may include, for example, a transceiver, a Power Amp Module (PAM), a frequency filter, or a Low Noise Amplifier (LNA). In addition, the RF unit 3034 may further include a component, such as a conductor or a conducting wire, for transmitting/receiving electromagnetic waves in the free space in radio communication. Although the cellular module 3021, the Wi-Fi module 3033, the BT module 3035, the GPS module 3037, and the NFC module 3039 share one RF module 3034 in FIG. 30, at least one of the cellular module 3021, the Wi-Fi module 3033, the BT module 3035, the GPS module 3037, and the NFC module 3039 may transmit/receive an RF signal through a separate RF module.

The SIM card 3014 may be inserted into a slot formed in a particular location of the electronic device. The SIM card 3014 may include unique identification information (e.g., Integrated Circuit Card IDentifier (ICCID)) or subscriber information (e.g., International Mobile Subscriber Identity (IMSI)).

The memory 3020 (e.g., the memory 1930) includes an internal memory 3022 or an external memory 3024. The internal memory 3022 includes at least one of a volatile memory (e.g., a Dynamic Random Access Memory (DRAM), a Static RAM (SRAM), a Synchronous Dynamic RAM (SDRAM), and the like) and a non-volatile memory (e.g., a One Time Programmable Read Only Memory (OTPROM), a Programmable ROM (PROM), an Erasable and Programmable ROM (EPROM), an Electrically Erasable and Programmable ROM (EEPROM), a mask ROM, a flash ROM, a NAND flash memory, a NOR flash memory, and the like).

The internal memory 3022 may be a Solid State Drive (SSD). The external memory 3024 may further include a flash drive, for example, a Compact Flash (CF), a Secure Digital (SD), a Micro Secure Digital (Micro-SD), a Mini Secure Digital (Mini-SD), an eXtreme Digital (xD), a memory stick, or the like. The external memory 3024 may be functionally connected to the electronic device 3000 through various interfaces. The electronic device 3000 may further include a storage device (or storage medium) such as a hard disc drive.

The sensor module 3040 measures a physical quantity or detects an operating state of the electronic device 3000 and converts the measured or detected information into an electric signal. The sensor module 3040 includes a gesture sensor 3040A, a gyro sensor 3040B, an atmospheric pressure sensor 3040C, a magnetic sensor 3040D, an acceleration sensor 3040E, a grip sensor 3040F, a proximity sensor 3040G, a color sensor 3040H (e.g., a Red, Green, Blue (RGB) sensor), a biometric sensor 3040I, a temperature/humidity sensor 3040J, an illumination sensor 3040K, and a UltraViolet (UV) sensor 3040M. Additionally or alternatively, the sensor module 3040 may include, for example, an E-nose sensor, an ElectroMyoGraphy (EMG) sensor, an ElectroEncephaloGram (EEG) sensor, an ElectroCardioGram (ECG) sensor, an InfraRed (IR) sensor, an iris scanner, and/or a fingerprint sensor. The sensor module 3040 may further include a control circuit for controlling at least one sensor included therein.

The input module 3050 includes a touch panel 3052, a digital pen sensor 3054, a key 3056, and an ultrasonic input device 3058. The touch panel 3052 recognizes a touch input through at least one of, for example, a capacitive type, a resistive type, an infrared type, and an ultrasonic type. In addition, the touch panel 3052 may further include a control circuit. For the capacitive type of touch panel, physical contact or proximity recognition is possible. The touch panel 3052 may further include a tactile layer. In this case, the touch panel 3052 may provide a tactile reaction to a user.

The digital pen sensor 3054 may be implemented, for example, using the same or a similar method to receiving a user's touch input or using a separate recognition sheet. The key 3056 may include, for example, a physical button, an optical key or a keypad. The ultrasonic input device 3058 detects acoustic waves with a microphone 3088 of the electronic device 3000 through an input tool for generating an ultrasonic signal to identify data, and wireless recognition is possible therethrough. The electronic device 3000 may also receive a user input from an external device (e.g., a computer or a server) connected thereto using the communication module 3030.

The display 3060 (e.g., the display 1950) may include a panel 3062, a hologram device 3064, or a projector 3066. The panel 3062 may be, for example, a Liquid Crystal Display (LCD), Active-Matrix Organic Light Emitting Diode (AM-OLED), or the like. The panel 3062 may be implemented to be, for example, flexible, transparent, or wearable. The panel 3062 may also be configured as one module together with the touch panel 3052. The hologram device 3064 shows a stereoscopic image in the air using interference of light. The projector 3066 projects light onto a screen to display an image. The screen may be located, for example, in the interior or on the exterior of the electronic device 3000. The display 3060 may further include a control circuit for controlling the panel 3062, the hologram unit 3064, or the projector 3066.

The interface 3070 includes, for example, a High-Definition Multimedia Interface (HDMI) 3072, a Universal Serial Bus (USB) 3074, an optical interface 3076, and a D-subminiature (D-sub) 3078. The interface 3070 may be included, for example, in the communication interface 1960 illustrated in FIG. 19. Additionally or alternatively, the interface 3070 may include, for example, a Mobile High-definition Link (MHL) interface, a Secure Digital (SD) card/Multi-Media Card (MMC) interface, or an Infrared Data Association (IrDA) standard interface.

The audio module 3080 bilaterally converts a sound and an electric signal. At least some elements of the audio module 3080 may be included, for example, in the input/output interface 1940 illustrated in FIG. 19. The audio module 3080 processes voice information input or output through, for example, a speaker 3082, a receiver 3084, earphones 3086, or the microphone 3088.

The camera module 3091 is a device that can take still and moving images, and may include one or more image sensors (e.g., a front sensor or a rear sensor), a lens, an Image Signal Processor (ISP), or a flash (e.g., an LED or a xenon lamp, not illustrated).

The power management module 3095 manages electric power of the electronic device 3000. The power management module 3095 may include, for example, a Power Management Integrated Circuit (PMIC), a charger Integrated Circuit (IC), or a battery or fuel gauge.

The PMIC may be mounted, for example, in integrated circuits or SoC semiconductors. The charging methods may be classified into wired charging and wireless charging. The charger IC may charge a battery and may prevent introduction of over-voltage or over-current from a charger. The charger IC may include a charger IC for at least one of the wired charging and the wireless charging. Examples of the wireless charging may include magnetic resonance charging, magnetic induction charging, and electromagnetic charging. An additional circuit, such as a coil loop, a resonance circuit, and a rectifier, may be added in order to implement the wireless charging.

The battery gauge may measure at least one of a residual quantity of the battery 3096, and a voltage, a current, or a temperature while charging. The battery 3096 stores or generates electricity and supplies power to the electronic device 3000 using the stored or generated electricity. The battery 3096 may include, for example, a rechargeable battery or a solar battery.

The indicator 3097 may display a particular state of the electronic device 3000 or a part thereof (e.g., the AP 3011), for example, a boot-up state, a message state, a charging state, or the like. The motor 3098 may convert an electric signal into mechanical vibration. Although not illustrated, the electronic device 3000 may include a processing unit (e.g., a Graphics Processing Unit (GPU)) for supporting mobile TV. The processing device for supporting mobile TV may process media data according to standards such as a Digital Multimedia Broadcasting (DMB), a Digital Video Broadcasting (DVB) or a media flow.

According to an embodiment of the present invention, a different respective disposable blood glucose tester for each manufacturer is produced as a standardized module to be detachably coupled to an electronic device, such as a smart phone, so that it is possible to change only the blood glucose measuring module with respect to the same electronic device.

In addition, according to an embodiment of the present invention, a display and a battery of an electronic device are used as a display and a battery for each disposable blood glucose tester, and independently provided parts (e.g., a chip, an electrode connector, and a circuit) are included in a separate modularized form and mounted to the electronic device, so that it is possible to produce a blood glucose tester in a replaceable form.

According to an embodiment of the present invention, a user can conveniently manage his/her blood glucose data using an application executed in an electronic device while continuing to use a disposable blood glucose strip model that the user usually uses. Furthermore, the user can easily measure and manage his/her blood glucose with only an electronic device, such as a smart phone, instead of using a separate blood glucose tester.

Each of the above described elements of an electronic device according to embodiments of the present invention may be formed of one or more components, and the name of a corresponding element may vary according to the type of an electronic device. An electronic device according to an embodiment of the present invention may include any of the above described elements, may exclude some of these elements, or may further include other additional elements. Further, some of the elements of an electronic device according to an embodiment of the present invention may be coupled to form a single entity while performing the same functions as those of the corresponding elements before the coupling.

At least some of the devices (e.g., modules or functions thereof) or methods (e.g., operations) according to embodiments of the present invention may be implemented by, for example, by a command stored in a non-transitory computer-readable storage medium in the form of a programming module. When the instruction is performed by at least one processor (e.g., the processor 210), the at least one processor may perform a function corresponding to the instruction. The non-transitory computer-readable storage medium may be, for example, the memory 220. At least some of the programming modules may be implemented (e.g., executed) by, for example, the processor 210. At least a part of the programming module may, for example, include a module, a program, a routine, a set of instructions, or a process for performing at least one function.

The non-transitory computer readable recording medium may include magnetic media such as a hard disc, a floppy disc, and a magnetic tape, optical media such as a Compact Disc-Read Only Memory (CD-ROM) and a Digital Versatile Disc (DVD), magneto-optical media such as a floptical disk, and hardware devices specifically configured to store and execute program commands, such as a Read Only Memory (ROM), a Random Access Memory (RAM), and a flash memory. In addition, the program instructions may include high class language codes, which can be executed in a computer by using an interpreter, as well as machine codes made by a compiler. The aforementioned hardware device may be configured to operate as one or more software modules in order to perform the operations of embodiments of the present invention, and vice versa.

Any of the modules or programming modules according to embodiments of the present invention may include at least one of the above described elements, exclude some of the elements, or further include other additional elements. The operations performed by the modules, programming module, or other elements according to embodiments of the present invention may be executed in a sequential, parallel, repetitive, or heuristic manner. Further, some operations may be executed in a different order, some of the operations may be omitted, or other operations may be added.

Although above-described embodiments of the present invention refers to blood glucose measurement as an example, embodiments of the present invention are not limited to blood-glucose measurement, but may be applied to other similar measurement strips and accompanying devices, including, but not limited to test strips and corresponding measurement devices for other biological or non-biological chemical samples. For example, embodiments of the present invention may be applied to test strips for urine or saliva. Further, embodiments of the present invention may be applied to tests for information other than glucose levels, such as testing for various chemicals or drugs, pregnancy, alcohol, pH levels, or other forms of tests. Although above-described embodiments of the present invention refer to distinguishing between different types of blood-glucose test strips, for example, embodiments of the present invention may also be applied to distinguishing between different types of test samples and or information to be detected. For example, embodiments of the present invention may be applied to distinguishing between strips for different types of blood tests (e.g., blood-glucose versus blood alcohol), and/or between strips between different types of samples, (e.g., blood versus urine).

According to embodiments of the present invention, in a storage medium that stores instructions, the instructions are set to allow at least one processor to perform at least one operation executed by the at least one processor including determining whether a strip for blood glucose measurement is inserted into a strip receiving part having a plurality of pins therein; identifying the type of strip for blood glucose measurement by at least one of the pins when the strip for blood glucose measurement is inserted; and applying a voltage configured in response to the identified type of strip to each pin of the strip receiving part.

While the present invention has been shown and described with reference to various embodiments thereof, it should be understood by those skilled in the art that many variations and modifications of the method and apparatus described herein will still fall within the spirit and scope of the present invention as defined in the appended claims and their equivalents.

What is claimed is:

1. A device for measuring blood glucose comprising:
a strip receiving part including a plurality of pins therein, the plurality of pins being arranged in such a manner that at least one of the plurality of pins contacts at least one electrode from among a plurality of electrodes formed in a blood glucose measurement strip when the blood glucose measurement strip is inserted into the strip receiving part, wherein the plurality of pins are arranged to be capable of identifying the blood glucose measurement strip corresponding to an electrode pattern by identifying pin numbers connected to the plurality of electrodes of the blood glucose measurement strip, wherein the plurality of pins include at least one first pin disposed on an inner side of the strip receiving part and at least one second pin disposed on an outer side of the strip receiving part;
a controller configured to:
identify whether the blood glucose measurement strip is completely inserted based on detecting a movement of the at least one first pin after a movement of the at least one second pin,
based on identifying that the blood glucose measurement strip is completely inserted, identify a type of the blood glucose measurement strip inserted into the strip receiving part by identifying which of the plurality of pins of the strip receiving part contacts the at least one electrode of the blood glucose measurement strip,
control application of a corresponding testing voltage configured in response to the identified type of the blood glucose measurement strip to at least one of the plurality of pins of the strip receiving part, and
measure a blood glucose value based on the corresponding testing voltage applied to the at least one of the plurality of pins of the strip receiving part and a reference value corresponding to the identified type of the blood glucose measurement strip; and
a connector that communicates with an external electronic device,
wherein the controller is configured to transmit the measured blood glucose value to the external electronic device.

2. The device of claim 1, wherein the controller is further configured to control application of an identification voltage for identifying the type of the blood glucose measurement strip to the at least one of the plurality of pins when the blood glucose measurement strip is inserted into the strip receiving part.

3. The device of claim 1, wherein the controller is further configured to identify the type of the blood glucose measurement strip in consideration of resistance values measured from the plurality of pins.

4. The device of claim 1, wherein the plurality of pins are moveable in a direction opposite to the protruding direction thereof as the blood glucose measurement strip is inserted into the strip receiving part, and
wherein the controller is further configured to identify whether the blood glucose measurement strip is inserted according to a detected movement of at least one of the plurality of pins.

5. The device of claim 1, wherein the controller is further configured to receive power from the external electronic device.

6. A method of measuring blood glucose by a device, comprising:
based on detecting a movement of at least one first pin after a movement of at least one second pin, identifying whether a blood glucose measurement strip is completely inserted into a strip receiving part having a plurality of pins therein, wherein the plurality of pins are arranged to be capable of identifying the blood glucose measurement strip corresponding to an electrode pattern by identifying pin numbers connected to a plurality of electrodes formed in the blood glucose measurement strip, wherein the plurality of pins include the at least one first pin disposed on an inner side of the strip receiving part and the at least one second pin disposed on an outer side of the strip receiving part;
based on identifying that the blood glucose measurement strip is completely inserted, identifying a type of the blood glucose measurement strip by at least one of the plurality of pins by identifying which of the plurality of pins of the strip receiving part contacts the at least one electrode of the blood glucose measurement strip when the blood glucose measurement strip is inserted;
applying a corresponding testing voltage configured in response to the identified type of the blood glucose measurement strip to at least one of the plurality of pins of the strip receiving part; and
measuring a blood glucose value based on the corresponding testing voltage applied to the at least one of the plurality of pins of the strip receiving part and a reference value corresponding to the identified type of the blood glucose measurement strip, wherein a connector of the device communicates with an external electronic device that is configured to receive the measured blood glucose value from the device.

7. The method of claim 6, further comprising:
applying an identification voltage for identifying the type of the blood glucose measurement strip to the at least one of the plurality of pins when the blood glucose measurement strip is inserted into the strip receiving part.

8. The method of claim 6, wherein the type of the blood glucose measurement strip is identified in consideration of resistance values measured from the plurality of pins.

9. The method of claim 6, wherein the plurality of pins are moveable in a direction opposite to the protruding direction thereof as the blood glucose measurement strip is inserted into the strip receiving part, and
wherein the method further comprises detecting movement of the plurality of pins to identify whether the blood glucose measurement strip is inserted.

10. An electronic device comprising:
a strip receiving part including a plurality of pins therein, the plurality of pins being arranged in such a manner that at least one of the plurality of pins contacts at least one electrode from among a plurality of electrodes formed in a blood glucose measurement strip when the blood glucose measurement strip is inserted into the strip receiving part, wherein the plurality of pins are arranged to be capable of identifying the blood glucose measurement strip corresponding to an electrode pattern by identifying pin numbers connected to the plurality of electrodes of the blood glucose measurement strip, wherein the plurality of pins include at least one first pin disposed on an inner side of the strip receiving part and at least one second pin disposed on an outer side of the strip receiving part;
a controller configured to:
identify whether the blood glucose measurement strip is completely inserted based on detecting a movement of the at least one first pin after a movement of the at least one second pin,
based on identifying that the blood glucose measurement strip is completely inserted, identify a type of the blood glucose measurement strip inserted into the strip receiving part by identifying which of the plurality of pins of the strip receiving part contacts the at least one electrode of the blood glucose measurement strip,
control application of a voltage configured in response to the identified type of the blood glucose measurement strip to at least one of the plurality of pins of the strip receiving part, and
measure a blood glucose value based on the voltage applied to the at least one of the plurality of pins of the strip receiving part and a reference value corresponding to the identified type of the blood glucose measurement strip;
a display unit configured to display information related to the measured blood glucose value; and
a connector that communicates with an external electronic device,
wherein the controller is configured to transmit the measured blood glucose value to the external electronic device.

11. The electronic device of claim 10, wherein the controller is further configured to control application of a voltage for identifying the type of the blood glucose measurement strip to the plurality of pins when the strip is inserted into the strip receiving part.

12. A casing of an electronic device, comprising:
a strip receiving part including a plurality of pins therein, the plurality of pins being arranged in such a manner that at least one of the plurality of pins contacts at least one electrode from among a plurality of electrodes formed in a blood glucose measurement strip when the blood glucose measurement strip is inserted into the strip receiving part, wherein the plurality of pins are arranged to be capable of identifying the blood glucose measurement strip corresponding to an electrode pattern by identifying pin numbers connected to the plurality of electrodes of the blood glucose measurement strip, wherein the plurality of pins include at least one first pin disposed on an inner side of the strip receiving part and at least one second pin disposed on an outer side of the strip receiving part;
a controller configured to:
identify whether the blood glucose measurement strip is completely inserted based on detecting a movement of the at least one first pin after a movement of the at least one second pin,
based on identifying that the blood glucose measurement strip is completely inserted, identify a type of the blood glucose measurement strip inserted into the strip receiving part by identifying which of the plurality of pins of the strip receiving part contacts the at least one electrode of the blood glucose measurement strip,
control application of a voltage configured in response to the identified type of the blood glucose measurement strip to at least one of the plurality of pins of the strip receiving part, and
measure a blood glucose value based on the voltage applied to the at least one of the plurality of pins of the strip receiving part and a reference value corresponding to the identified type of the blood glucose measurement strip; and
a communication unit configured to transmit blood glucose related information including the measured blood glucose value to the electronic device when the casing is coupled to the electronic device.

13. The casing of claim 12, further comprising:
a first rear cover that is coupled to the rear surface of the electronic device and provided with the controller; and
a second rear cover that is coupled to the first rear cover and has a storage section formed in a space which the first and second rear covers form when being coupled to each other, wherein the storage section accommodates a tool related to the measuring of the blood glucose value.

14. A device for checking a chemical strip comprising:
a strip receiving part including a plurality of pins therein, the plurality of pins being arranged in such a manner that at least one of the plurality of pins contacts at least one electrode from among a plurality of electrodes formed in the chemical strip when the chemical strip is inserted into the strip receiving part, wherein the plurality of pins are arranged to be capable of identifying the chemical strip corresponding to an electrode pattern by identifying pin numbers connected to the plurality of electrodes of the chemical strip, wherein the plurality of pins include at least one first pin disposed on an inner side of the strip receiving part and at least one second pin disposed on an outer side of the strip receiving part;
a controller configured to:

identify whether the blood glucose measurement strip is completely inserted based on detecting a movement of the at least one first pin after a movement of the at least one second pin, based on identifying that the blood glucose measurement strip is completely inserted, identify a type of the chemical strip inserted into the strip receiving part by identifying which of the plurality of pins of the strip receiving part contacts the at least one electrode of the chemical strip, control an application of a corresponding testing voltage configured in response to the identified type of the chemical strip to at least one of the plurality of pins of the strip receiving part, and measure a blood glucose value based on the corresponding testing voltage applied to the at least one of the plurality of pins of the strip receiving part and a reference value corresponding to the identified type of the chemical strip; and a connector that communicates with an external electronic device, wherein the controller is configured to transmit the measured blood glucose value to the external electronic device.

15. A casing of an electronic device, comprising:

a strip receiving part including a plurality of pins therein, the plurality of pins being arranged in such a manner that at least one of the plurality of pins contacts at least one electrode from among a plurality of electrodes formed in a blood glucose measurement strip when the blood glucose measurement strip is inserted into the strip receiving part, wherein the plurality of pins are arranged to be capable of identifying the blood glucose measurement strip corresponding to an electrode pattern by identifying pin numbers connected to the plurality of electrodes of the blood glucose measurement strip; and a controller configured to:

detect, from the blood glucose measurement strip, first information that is differentiated according to a type of the blood glucose measurement strip by identifying which of the plurality of pins of the strip receiving part contacts the at least one electrode of the blood glucose measurement strip, and a communication unit configured to transmit, to the electronic device, the detected information differentiated according to the type of the blood glucose measurement strip and to receive, from the electronic device, second information indicating a corresponding voltage to be applied according to the type of the blood glucose measurement strip, wherein the controller is configured to apply the corresponding voltage to each pin of the strip receiving part according to the second information and measure the blood glucose level based on the corresponding voltage applied to at least one of the plurality of pins of the strip receiving part and a reference value corresponding to the identified type of the blood glucose measurement strip.

* * * * *